(12) United States Patent
Walker et al.

(10) Patent No.: US 11,639,499 B1
(45) Date of Patent: May 2, 2023

(54) REVERSE TRANSCRIPTASE VARIANTS

(71) Applicant: Watchmaker Genomics, Inc., Boulder, CO (US)

(72) Inventors: Julie Walker, Wheat Ridge, CO (US); Bjarne Faurholm, Cape Town (ZA); Ross Wadsworth, Cape Town (ZA); Brian A. Kudlow, Boulder, CO (US)

(73) Assignee: Watchmaker Genomics, Inc., Boulder, CO (US)

( * ) Notice: Subject to any disclaimer, the term of this patent is extended or adjusted under 35 U.S.C. 154(b) by 0 days.

(21) Appl. No.: 17/940,797

(22) Filed: Sep. 8, 2022

Related U.S. Application Data

(60) Provisional application No. 63/317,634, filed on Mar. 8, 2022.

(51) Int. Cl.
*C12N 9/12* (2006.01)

(52) U.S. Cl.
CPC .... *C12N 9/1276* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 6,210,891 B1 | 4/2001 | Nyren et al. | |
| 6,306,597 B1 | 10/2001 | Macevicz | |
| 6,828,100 B1 | 12/2004 | Ronaghi | |
| 6,833,246 B2 | 12/2004 | Balasubramanian | |
| 6,911,345 B2 | 6/2005 | Quake et al. | |
| 7,232,656 B2 | 6/2007 | Balasubramanian et al. | |
| 7,598,035 B2 | 10/2009 | Macevicz | |
| 7,835,871 B2 | 11/2010 | Kain et al. | |
| 7,960,120 B2 | 6/2011 | Rigatti et al. | |
| 8,209,130 B1 | 6/2012 | Kennedy et al. | |
| 2006/0024681 A1 | 2/2006 | Smith et al. | |
| 2006/0292611 A1 | 12/2006 | Berka et al. | |
| 2007/0114362 A1 | 5/2007 | Feng et al. | |
| 2011/0009278 A1 | 1/2011 | Kain et al. | |

OTHER PUBLICATIONS

Baba et al. (Further increase in thermostability of Moloney murine leukemia virus reverse transcriptase by mutational combination, Protein Engineering, Design & Selection, 2017, vol. 30 No. 8, pp. 551-557).*

Karlsson, 2016, Counting Molecules in cell-free DNA and single cells RNA, Karolinska Institute, 52 pages.

* cited by examiner

*Primary Examiner* — Suzanne M Noakes
*Assistant Examiner* — Jae W Lee
(74) *Attorney, Agent, or Firm* — Withers Bergman, LLP; Thomas C. Meyers

(57) ABSTRACT

The present invention provides MMLV reverse transcriptase enzymes with increased thermal stability as compared with wild type MMLV and AMV reverse transcriptases. The improved thermal stability allows for reverse transcription of RNA to cDNA at temperatures above 37° C., thereby reducing error rates introduced during cDNA synthesis. As a result, the reverse transcriptases of the invention allow for increased accuracy in the determination of transcriptomes of living organisms.

18 Claims, 14 Drawing Sheets

Specification includes a Sequence Listing.

| RT | FSS temp | Efficiency score |
|---|---|---|
| WMG RTIII | 50 | 96 |
| WMG RTIII | 60 | 99 |
| prod-ana RT | 50 | 92 |
| prod-ana RT | 60 | 99 |
| Maxima | 50 | 125 |
| Maxima | 60 | 160 |

FIG. 1B

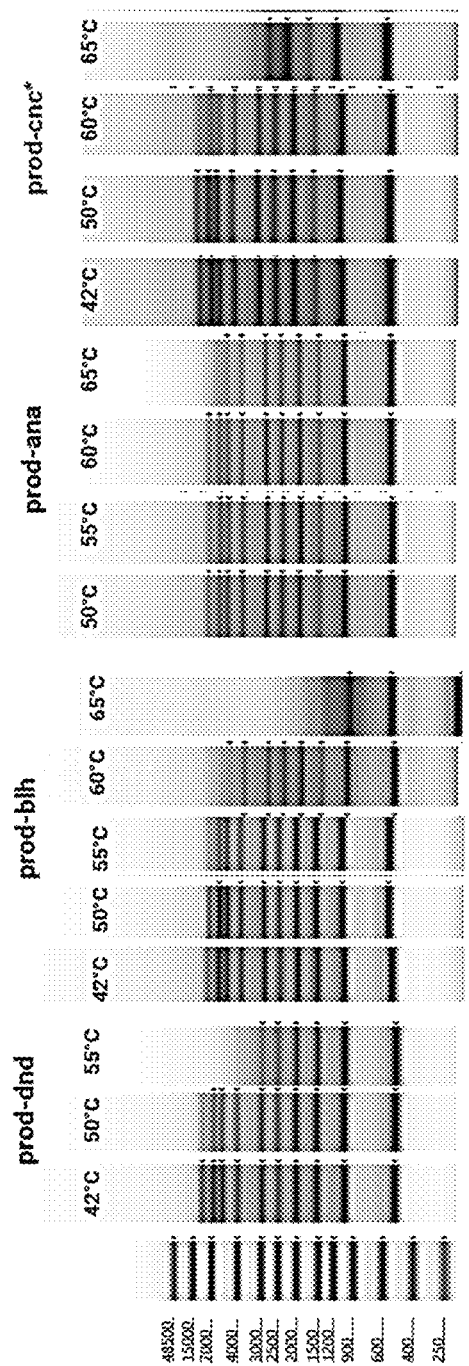
Figure 2B - Processivity at elevated temperatures

| IP name | Tagg (C) | % CV |
|---|---|---|
| prod-dnd | 60.7 | 0.25 |
| prod-amg | 61.6 | 0.08 |
| prod-ajw | 62.9 | 0.1 |
| prod-blh | 63.1 | 0.68 |
| prod-cnc* | 65.9 | 0.67 |
| prod-ana | 68.2 | 0.69 |

FIG. 3D

Delta Ct values for guanidine isothiocyanate (Ct inhibitor - Ct no inhibitor)

REVERSE TRANSCRIPTASE VARIANTS

TECHNICAL FIELD

The present invention relates to reverse transcriptases.

SEQUENCE LISTING

This application contains a sequence listing which has been submitted in eXtensible Markup Language (XML) format via the Patent Center and is hereby incorporated by reference in its entirety. The XML-formatted sequence listing, created on Sep. 9, 2022, is named WMG-005-01US-ST26.xml, and is 31,146 bytes in size.

BACKGROUND

The transcriptome refers to the RNA transcripts of a cell or organism at a given time. Knowledge of the transcriptome reveals active cellular processes and can provide information about cell regulation, growth and dysfunction.

Transcriptome analysis typically involves microarray technology and, more commonly, next-generation sequencing technologies (e.g., RNA-Seq). Common objectives of RNA-Seq are to detect all of the diverse transcripts present, including mRNA and non-coding RNA, as well as to detect splice variants, mutations, mobile genetic elements, and expression levels during various stages of development or under various conditions. Transcriptomics and RNA-Seq have application in diagnostics, disease profiling, pathogen detection, evolutionary biology, and other areas of research. For example, RNA-Seq can potentially identify genes involved in resistance to environmental stresses, such as drought resistance in crops. In another example, transcriptomic profiling can provide information on mechanisms of drug resistance, potentially revealing strategies for combating hospital-acquired antibiotic-resistant infections.

Typically, in an RNA-Seq workflow, RNA is first used to synthesize stable complementary DNA (cDNA) copies of target RNA through a reverse transcription reaction. Reverse transcriptase enzymes are the typical enzymes used to synthesize cDNA from an RNA. Because reverse transcriptases have no proofreading ability, unlike DNA polymerases, higher reaction temperatures for reverse transcription reactions are generally desirable. This is because the higher temperatures reduce off-target primer binding. In addition, higher temperatures reduce secondary structures in RNA, which can cause steric hinderance to the RT, thus truncating transcripts. However, common commercially available reverse transcriptases, for example Moloney murine leukemia virus (MMLV), Superscript II, and avian myeloblastosis virus (AMV), begin to lose efficiency above 37° C. As a result, the high error rate allows mutations to accumulate at an accelerated rate in comparison to proofread forms of synthesis. For example, AMV reverse transcriptases typically have error rates of 1 in 17,000 bases and MMLVs typically have errors rates of 1 in 30,000 bases. As a result, commercially available reverse transcriptases impede accurate determination of a transcriptome.

SUMMARY

The present invention provides modified reverse transcriptase enzymes with increased thermal stability, increased solubility and reduced qPCR inhibition as compared with conventional commercial reverse transcriptases, such as, for example, the Superscript II reverse transcriptase (shown herein as prod-dnd, SEQ ID NO: 2). The improved thermal stability allows for reverse transcription of RNA to cDNA at temperatures above 37° C., thereby reducing error rates introduced during cDNA synthesis. As a result, the reverse transcriptases of the invention allow for increased accuracy in transcriptomics.

Reverse transcriptases of the invention may comprise a polypeptide comprising a sequence of amino acids having at least about 95% sequence identity with the reverse transcriptase of SEQ ID NO: 2, and at least one amino acid substitution at an amino acid position selected from positions 56, 72, 138, 163, 232, 234, 249, 290, 344, 420, 424, 444, and 615.

The at least one amino acid substitution may be selected from:

S at position 56 substituted with G, A, V, L, or I;
  G at position 138 substituted with S, C, T, or M;
  S at position 232 substituted with C, T, or M;
  L at position 234 substituted with D, E, N, Q;
  G at position 290 substituted with H, K, or R;
  Y at position 344 substituted with F or M;
  T at position 420 substituted with G, A, V, L, or I;
  G at position 424 substituted with D, E, N, Q;
  V at position 444 substituted with G, A, L, or I; and
  D at position 615 substituted with E, N, or Q.

For example, at least one amino acid substitution may be S56A, G138S, S232T, L234E, G290K, Y344F, T420V, G424D, V444I, and D615E. In addition, any of the following are examples of mutations according to the invention: S27T, V43K, A46P, L48I, A54P, S56A, S60W, Q68K, L72Q/R, E123Q, Y133C, G138S, T163K, M177R, D200H, I212T, I218T, T231E, S232T, L234E, Q237E, A242D, N249E, Q265E, K264Q, K267T, L272I, T281S, G290K, N335Q, P338E, D339E, Y344F, Q345D E346D, Q349R, Y376F, V413I, T420V, G424D, A442S, V433T, V444I, D518E, G524D, L528F, A554P, Q562E, D583N, K550S, D615E, A619E, F625W/H, R629K, H642D, and K658E.

A reverse transcriptase of the invention further comprises at least one additional amino acid substitution at an amino acid position selected from positions 524, 583, and 562. The additional amino acid substitution may be selected from:

D at position 524 substituted with G, A V, L, or I;
  D at position 583 substituted with E, N, or Q; and
  E at position 562 substituted with D, N, or Q.

For example, the at least one additional amino acid substitution may be selected from D524G, D583N, and E562Q.

In some embodiments, a reverse transcriptase comprises any number of substitutions from among positions 56, 138, 234, 290, 344, 420, 424, 444, 615, 524, 583, and 562. For example, the reverse transcriptase may comprise substitutions in at least 3 amino acid positions selected from positions 56, 138, 234, 290, 344, 420, 424, 444, 615, 524, 583, and 562. The reverse transcriptase may comprise substitutions in at least 5 amino acid positions selected from positions 56, 138, 234, 290, 344, 420, 424, 444, 615, 524, 583, and 562. The reverse transcriptase may comprise substitutions in at least 10 amino acid positions selected from positions 56, 138, 234, 290, 344, 420, 424, 444, 615, 524, 583, and 562. The reverse transcriptase may comprise substitutions in 12 amino acid positions selected from positions 56, 138, 234, 290, 344, 420, 424, 444, 615, 524, 583, 562.

In aspects of the invention, reverse transcriptases of the invention comprise a polypeptide comprising a sequence of amino acids having at least about 95% sequence identity with the reverse transcriptase of SEQ ID NO: 2, and at least one amino acid substitution at an amino acid position selected from positions 56, 138, 234, 290, 344, 420, 424, 444, 615, and 642.

The at least one amino acid substitution is selected from:
S at position 56 substituted with G, A, V, L, or I;
G at position 138 substituted with S, C, T, or M;
L at position 234 substituted with D, E, N, or Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I;
D at position 615 substituted with E, N, or Q; and
H at position 642 substituted with D, E, N, or Q.

For example, the at least one amino acid substitution may be selected from S56A, G138S, S232T, L234E, G290K, Y344F, T420V, G424D, V444I, D615E, and H642D.

The reverse transcriptase may further comprise at least one additional amino acid substitution at an amino acid position selected from positions 524, 583, 562, 204, and 306.

The at least one additional amino acid substitution may be selected from:
D at position 524 substituted with G, A V, L, or I;
D at position 583 substituted with E, N, or Q;
E at position 562 substituted with D, N, or Q;
H at position 204 substituted with K or R; and
T at position 306 substituted with H, K, or R.

For example, the additional amino acid substitution may be G524D, N583D, Q562E, R204H, or K306T.

Reverse transcriptase of the present invention exhibit increased thermal stability relative to both wild type reverse transcriptases as well as common commercial reverse transcriptases, such as Superscript II (SEQ ID NO: 2). For example, reverse transcriptases of the invention at 50° C. have at least about 50% of the reverse transcription activity of either the wild type reverse transcriptase or the reverse transcriptase of SEQ ID NO: 2 at 42° C. However, depending on the number of mutations and conditions, at 50° C. or greater the activity of a reverse transcriptase of the invention may even exceed about 90% of the reverse transcription activity of either the wild type reverse transcriptase or the reverse transcriptase of SEQ ID NO: 2 at 42° C. For example, when 10 or more mutations are present, the reverse transcription activity exceeds 80% of the reverse transcription activity of the reverse transcriptase of SEQ ID NO: 2 at 42° C.

Further the activity of reverse transcriptases of the invention exceeds physiological activity of, for example, a reverse transcriptase as shown in SEQ ID NO: 2, at even higher temperatures, for example, 65° C. For example, a reverse transcriptase of the invention at temperatures of about 65° C. or greater shows at least 50% of the reverse transcription activity of the reverse transcriptase of SEQ ID NO: 2 at 42° C. In contrast, the reverse transcriptase activity of either a wild type transcriptase or that shown in SEQ ID NO: 2 would be considerably inhibited at temperatures above about 50° C. and nearly inactive at temperatures approaching about 65° C. Again, however, depending on the number of mutations and conditions, at about 65° C. or greater the reverse transcription activity of a reverse transcriptase of the invention may even exceed 80% of the reverse transcription activity of either the reverse transcriptase shown in SEQ ID NO: 2 or the wild type reverse transcriptase at 42° C. For example, when 10 or more mutations are present, the reverse transcription activity may exceed 70% of the reverse transcription activity of either the wild type reverse transcriptase or the reverse transcriptase shown in SEQ ID NO: 2 at 42° C.

Reverse transcriptases of the invention have improved activity compared to conventional commercial reverse transcriptases, including wild type reverse transcriptase, in the presence of inhibitors. Various inhibitors are found in a variety of samples that cause wild type and commercially-available reverse transcriptases to perform inefficiently. For example, plant samples typically contain polysaccharides, phenolics, and flavonoids that inhibit reverse transcription. Sample preparation steps also frequently introduce reverse transcription inhibitors, for example detergents, alcohols, salts, heparin, and hematin.

The present invention further provides methods of reverse transcribing cDNA from RNA using a reverse transcriptase of the invention.

Preferred methods of the invention comprise the steps of providing to a sample comprising RNA a reverse transcriptase comprising a polypeptide comprising a sequence of amino acids having at least about 95% sequence identity with the reverse transcriptase of SEQ ID NO: 2, and at least one amino acid substitution at an amino acid position selected from positions 56, 138, 234, 290, 344, 420, 424, 444, and 615; and reagents for reverse transcription. The methods further comprise the step of performing a reverse transcription reaction between the reverse transcriptase and the RNA in the sample to form cDNA.

The at least one amino acid substitution may be selected from:
S at position 56 substituted with G, A, V, L, or I;
G at position 138 substituted with S, C, T, or M;
S at position 232 substituted with C, T, or M;
L at position 234 substituted with D, E, N, Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I; and
D at position 615 substituted with E, N, or Q.

For example, the at least the at least one amino acid substitution may be S56A, G138S, S232T, L234E, G290K, Y344F, T420V, G424D, V444I, and D615.

The reverse transcriptase may further comprise at least one additional amino acid substitution at an amino acid position selected from positions 524, 583, and 562. The at least one additional amino acid substitution may be selected from:
D at position 524 substituted with G, A V, L, or I;
D at position 583 substituted with E, N, or Q; and
E at position 562 substituted with D, N, or Q.

In one example, the additional amino acid substitution is selected from G524D, N583d, and Q562E.

The reverse transcriptase may comprise any number of substitutions from among positions 56, 138, 234, 290, 344, 420, 424, 444, 615, 524, 583, and 562. For example, the reverse transcriptase may comprise substitutions in at least 3 amino acid positions selected from positions 56, 138, 234, 290, 344, 420, 424, 444, 615, 524, 583, and 562. The reverse transcriptase may comprise substitutions in at least 5 amino acid positions selected from positions 56, 138, 234, 290, 344, 420, 424, 444, 615, 524, 583, and 562. The reverse transcriptase may comprise substitutions in at least 10 amino acid positions selected from positions 56, 138, 234, 290, 344, 420, 424, 444, 615, 524, 583, and 562. The reverse transcriptase may comprise substitutions in 13 amino acid positions selected from positions 56, 138, 234, 290, 344, 420, 424, 444, 615, 524, 583, 562.

In aspects of the invention, reverse transcriptases of the invention comprise a sequence of amino acids having at least about 95% sequence identity with the reverse transcriptase of SEQ ID NO: 2, and at least one amino acid substitution at an amino acid position selected from positions 56, 138, 234, 290, 344, 420, 424, 444, 615. 444, 615, and 642.

The at least one amino acid substitution is selected from:
S at position 56 substituted with G, A, V, L, or I;
G at position 138 substituted with S, C, T, or M;
S at position 232 substituted with C, T, or M;
L at position 234 substituted with D, E, N, or Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I;
D at position 615 substituted with E, N, or Q; and
H at position 642 substituted with D, E, N, or Q.

For example, the amino acid substitution may be selected from S56A, G138S, S232T, L234E, G290K, Y344F, T420V, G424D, V444I, D615E, and H642D.

The reverse transcriptase may further comprise at least one additional amino acid substitution at an amino acid position selected from positions 524, 583, 562, 204, and 306.

The additional amino acid substitution may also be selected from:
D at position 524 substituted with G, A V, L, or I;
D at position 583 substituted with E, N, or Q;
E at position 562 substituted with D, N, or Q;
H at position 204 substituted with K or R; and
T at position 306 substituted with H, K, or R.

In one alternative, the additional amino acid substitution is selected from G524D, N583D, Q562E, R204H, and K306T.

Use of reverse transcriptases of the invention allows reactions to occur at a temperature of 50° C. or greater without the loss of enzyme activity that would occur with conventional reverse transcriptases. Accordingly, the performing step may be conducted at a temperature of about 65° C. or greater with an activity of at least about 50% of the activity of the reverse transcriptase shown in SEQ ID NO: 2 at 42° C. Due to the increased thermostability of the reverse transcriptases of the invention, the increased reaction temperature allows for both highly active reverse transcriptase activity and reduced nucleotide base addition errors in cDNA synthesis. Moreover, the reverse transcription reaction may result in a reduced incubation time, for example the incubation time may be about 5, 10, 15, 20, or 30 minutes, in comparison to typical methods requiring 50 minutes.

Aspects of the invention provide modified reverse transcriptases comprising at least one mutation in at least one domain of the reverse transcriptase of SEQ ID NO: 2. Importantly, the modified reverse transcriptases of the invention exhibit increased thermal stability relative to either the wild type reverse transcriptase or that shown in SEQ ID NO: 2 such that the activity of the reverse transcriptase at temperatures of about 50° C. or greater is at least about 90% of the activity of the transcriptase of SEQ ID NO: 2 at 42° C.

Preferred mutations include an amino acid substitution at position 27, 138, 200, 204, 212, 218, 231, 232, 234, 237, 242, 249, 264, 265, 267, and/or 272 in the palm domain of SEQ ID NO: 2. In addition, the invention contemplates mutations at positions 43, 46, 48, 54, 56, 72, 163, and/or 177 in the finger domain of the; positions 280, 281, 290, 306, 335, 338, 339, 344, 345, 346, and/or 349 in the thumb domain; positions 376, 413, 420, 424, 443, and/or 444 in the connection domain, and/or positions 518, 524, 528, 550, 554, 562, 583, 615, 619, 625, 629, 642, and/or 658 in the RNAse H domain of SEQ ID NO: 2.

Below is a list of preferred substitution mutation for use in the invention:
S at position 56 substituted with G, A, V, L, or I;
L at position 72 substituted with Q or R;
G at position 138 substituted with S, C, T, or M;
H at position 204 substituted with K or R;
S at position 232 substituted with C, T, or M;
L at position 234 substituted with D, E, N, Q;
G at position 290 substituted with H, K, or R;
T at position 306 substituted with H, K, or R
Y at position 344 substituted with F or M;
T at position 420 substituted with G, A, V, L, or I;
G at position 424 substituted with D, E, N, or Q;
V at position 444 substituted with G, A, L, or I;
D at position 524 substituted with G, A V, L, or I;
E at position 562 substituted with D, N, or Q;
D at position 583 substituted with E, N, or Q;
D at position 615 substituted with E, N, or Q; and
H at position 642 substituted with D, E, N, or Q.

A modified reverse transcriptase of the invention may have substitutions in one to 14 amino acid positions selected from positions 56, 72, 138, 204, 232, 234, 290, 306, 344, 420, 424, 444, 524, 562, 583, 615, and 642.

In addition, preferred amino acid substitutions include S56A, G138S, S232T, L234E, G290K, Y344F, T420V, G424D, V444I, and/or D615E. In addition to the foregoing, an additional amino acid substitution selected from G524d, N583D, and Q562E may be added. In other embodiments, the amino acid substitution is selected from L72Q, T163K, N249E, and H642D. In still other embodiments, the amino acid substitution is selected from S56A, G138S, S232T, L234E, G290K, Y344F, T420V, G424D, V444I, D615E, and H642D. That embodiment may also include at least one additional amino acid substitution selected from D524G, D583N, E562Q, H204R, and T306K.

In specific embodiments, the amino acid substitutions is selected from S27T, V43K, A46P, L48I, A54P, S56A, L72Q, G138S, T163K, M177R, D200H, I212T, I218T, T231E, S232T, L234E, Q237E, A242D, N249E, Q265E, K264Q, K267T, L272I T281S, G290K, N335Q P338E, D339E, Y344F, Q345D E346D, Q349R, Y376F, V413I, T420V, G424D, A442S, V433T, V444I, D518E, G524D, L528F, A554P, E562Q, D583N, K550S, D615E, A619E, F625W/H, R629K, H642D, and K658E with respect to SEQ ID NO: 2.

In preferred embodiments, a modified reverse transcriptase of the invention demonstrates enzymatic activity at temperatures of about 65° C. or greater that is equivalent to at least about 50% of the reverse transcription activity of the reverse transcriptase shown in SEQ ID NO: 2 at about 42° C. The activity of a reverse transcriptase of the invention is improved in the presence of inhibitors. Additionally, modified reverse transcriptases of the invention exhibit increased thermal stability relative to a reverse transcriptase of SEQ ID NO: 2 and may include at least one amino acid substitution selected from the group consisting of E5K; M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

Specifically, activity of a reverse transcriptase of the invention is improved in the presence of inhibitors relative to a reverse transcriptase shown in SEQ ID NO: 2 and may include at least one amino acid substitution selected from the group consisting of M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

In other embodiments, a reverse transcriptase of the invention exhibits improved activity in formalin-fixed samples relative to a reverse transcriptase of SEQ ID NO: 2 and may include at least one amino acid substitution selected from the group consisting of M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

In still other embodiments, a reverse transcriptase of the invention exhibits increased thermal stability relative to a reverse transcriptase of SEQ ID NO: 2 and may include at least one amino acid substitution selected from the group consisting of A32V, E286R, E302K, W388R, and L435R.

Activity of reverse transcriptases of the invention in the presence of inhibitors is also improved relative to the reverse transcriptase of SEQ ID NO: 2 and may include at least one amino acid substitution selected from the group consisting of A32V, E286R, E302K, W388R, and L435R. Likewise, the reverse transcription activity of reverse transcriptases of the invention is improved in formalin-fixed samples relative to a reverse transcriptase of SEQ ID NO: 2 and may include at least one amino acid substitution selected from the group consisting of A32V, E286R, E302K, W388R, and L435R.

In certain embodiments, modified reverse transcriptases of the invention have at least about 95% sequence identity with respect to the reverse transcriptase shown in SEQ ID NO: 2.

Aspects of the invention include methods of reverse transcribing cDNA from RNA. Such methods include utilizing a modified reverse transcriptase as provided herein. Such modified enzymes exhibit improved thermal stability relative to existing reverse transcriptase such that their activity at temperatures of about 50° C. or greater is at least about 90% of the reverse transcription activity of conventional reverse transcriptases at 42° C. and providing to the sample reagents for reverse transcription, and performing a reverse transcription reaction between the reverse transcriptase and the RNA in the sample. The reverse transcription reaction is conducted at a temperature of 50° C. or greater to form the cDNA.

Modified enzymes of the invention comprise at least one amino acid substitution at a position selected from positions 27, 138, 200, 204, 212, 218, 231, 232, 234, 237, 242, 249, 264, 265, 267, and 272 in a palm domain of the reverse transcriptase shown in SEQ ID NO: 2, positions 43, 46, 48, 54, 56, 72, 163, and 177 in a finger domain of SEQ ID NO: 2, positions 280, 281, 290, 306, 335, 338, 339, 344, 345, 346, and 349 in a thumb domain of SEQ ID NO: 2, positions 376, 413, 420, 424, 443, and 444 in a connection domain of SEQ ID NO: 2, and positions 518, 524, 528, 550, 554, 562, 583, 615, 619, 625, 629, 642, and 658 in the RNAse H domain of the reverse transcriptase shown in SEQ ID NO: 2.

For example, the amino acid substitution may be selected from:

S at position 56 substituted with G, A, V, L, or I;
L at position 72 substituted with Q or R;
G at position 138 substituted with S, C, T, or M;
H at position 204 substituted with K or R;
S at position 232 substituted with C, T, or M;
L at position 234 substituted with D, E, N, Q;
G at position 290 substituted with H, K, or R;
T at position 306 substituted with H, K, or R
Y at position 344 substituted with F or M;
T at position 420 substituted with G, A, V, L, or I;
G at position 424 substituted with D, E, N, or Q;
V at position 444 substituted with G, A, L, or I;
D at position 524 substituted with G, A V, L, or I;
E at position 562 substituted with D, N, or Q;
D at position 583 substituted with E, N, or Q;
D at position 615 substituted with E, N, or Q; and
H at position 642 substituted with D, E, N, or Q.

Modified reverse transcriptases of the invention may comprise substitutions in at least 3 amino acid positions up to at least 12 amino acid positions, wherein the amino acid positions are selected from positions 56, 72, 138, 204, 232, 234, 290, 306, 344, 420, 424, 444, 524, 562, 583, 615, and 642. Specifically, the amino acid substitution may be selected from S56A, G138S, S232T, L234E, G290K, Y344F, T420V, G424D, V444I, and D615E. In certain embodiments, the modified reverse transcriptases may comprise at least one additional amino acid substitution selected from G524D, N583D, and Q562E. The at least one amino acid substitution may be selected from L72Q, T163K, N249E, and H642D. Additionally and/or alternatively, the amino acid substitution is selected from S56A, G138S, S232T, L234E, G290K, Y344F, T420V, G424D, V444I, D615E, and H642D. This embodiment may further comprise additional amino acid substitution selected from D524G, D583N, E562Q, H204R, and T306K.

Methods of the invention may further comprise any known reagents and methods for reverse transcription. For example, the providing step may comprise providing to the sample capture oligos that capture target RNA molecules.

BRIEF DESCRIPTION OF THE DRAWINGS

FIG. 1B gives efficiency scores for the enzymes.

FIG. 2B shows processivity of RT enzymes of embodiments of the disclosure at elevated temperatures.

FIG. 3D shows a table of results for the thermal ramp assay of FIG. 3C.

DETAILED DESCRIPTION

Figure 1A:
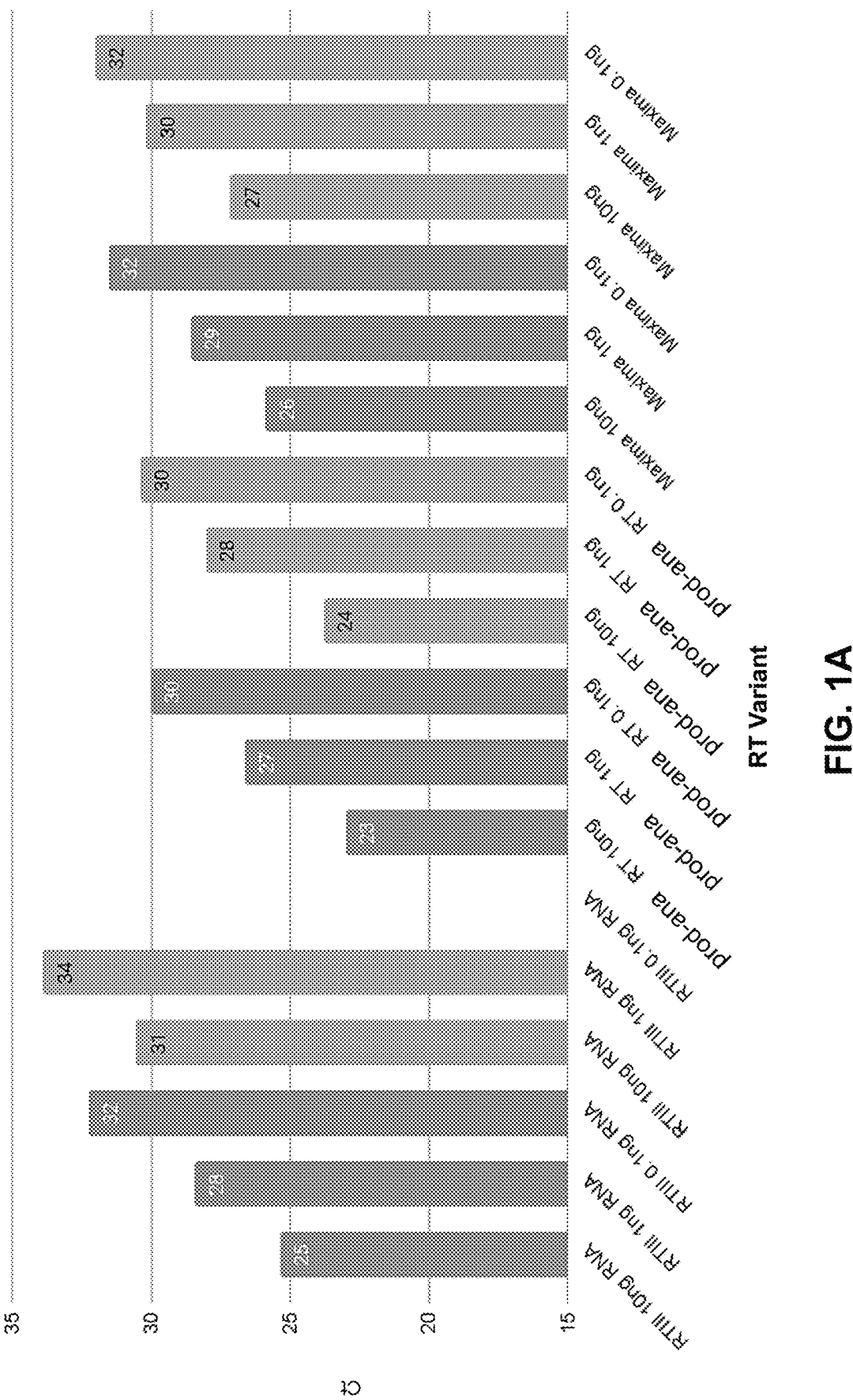
FIG. 1A gives qPCR results showing thermo-activity of RT enzymes of the disclosure.

The present invention provides reverse transcriptase enzymes with increased thermal stability as compared to conventional reverse transcriptases, such as Superscript II (SEQ ID NO: 2) or the wild type reverse transcriptase shown in SEQ ID NO: 1. The improved thermal stability allows for reverse transcription of RNA to cDNA at temperatures above about 42° C., thereby reducing error rates introduced during cDNA synthesis. As a result, the reverse transcriptases of the invention allow for increased accuracy in the determination of transcriptomes of living organisms.

Specifically, disclosed are modified reverse transcriptases that comprise substitutions at least one position in SEQ ID NO: 2 selected from positions 56, 72, 138, 163, 234, 249, 290, 344, 420, 424, 444, 615, 642, 524, 583, 562, 204, and 306. For example, the amino acid substitutions may be:

S at position 56 substituted with G, A, V, L, or I;
G at position 138 substituted with S, C, T, or M;
S at position 232 substituted with C, T, or M;
L at position 234 substituted with D, E, N, or Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I;
D at position 615 substituted with E, N, or Q;
H at position 642 substituted with D, E, N, or Q.
D at position 524 substituted with G, A V, L, or I;
D at position 583 substituted with E, N, or Q;
E at position 562 substituted with D, N, or Q;
H at position 204 substituted with K or R; and
T at position 306 substituted with H, K, or R.

The invention recognizes that increased temperatures during reverse transcription reactions reduces non-target primer binding, error rates in cDNA synthesis and reduces RNA secondary structures. Accordingly, the improved thermal stability of the reverse transcriptases of the invention allows for reverse transcription of RNA to cDNA at temperatures above 37° C., the optimal temperature for wild type and other conventional reverse transcriptases. By allowing for an increased reaction temperature, reverse transcriptases of the invention result in reduced error rates in cDNA synthesis.

Moreover, the reverse transcriptases of the present invention provide additional advantages over wild type and other conventional reverse transcriptases, including improved efficiency in the presence of inhibitors or reverse transcriptase and improved efficiency in formalin-fixed samples.

Reverse Transcription

Reverse transcription is the synthesis of DNA from an RNA template and produces cDNA. Reverse transcriptases use an RNA template and a short primer complementary to the 3' end of the RNA to direct the synthesis of the first strand cDNA, which can be used directly as a template for the Polymerase Chain Reaction (PCR). This combination of reverse transcription and PCR allows the detection of RNA in a sample and production of the corresponding cDNA. RNase H activity, from either the reverse transcriptase or supplied exogenously, may be used to separate RNA/cDNA hybrids. Further components may also include buffers, one or more primers, a dNTP Mix (a mix of the nucleotides dATP, dCTP, dGTP and dTTP), agents needed for PCR, synthesis of a second DNA strand, or amplification reagents.

Reverse transcription may be performed by capture oligos that have a free, 3' poly-T region. The 3' portions of the capture oligos may include target-specific sequences or oligomers, for example capture primers to reverse transcribe RNA molecules comprising the capture sequence. The oligomers may be random or "not-so-random" (NSR) oligomers (NSROs), such as random hexamers or NSR hexamers. The oligos may include one or more handles such as primer binding sequences cognate to PCR primers that are used in the amplifying step or the sequences of NGS sequencing adaptors. The reverse transcription primers may include template switching oligos (TSOs), which may include poly-G sequences that hybridize to and capture poly-C segments added during reverse transcription.

Reverse transcription of RNA may comprise use of a capture sequence and a capture primer or probe. Primer sequences may comprise a binding site, for example a primer sequence that would be expected to hybridize to a complementary sequence in a nucleic acid molecule. The primer sequence may also be a "universal" primer sequence, i.e. a sequence that is complementary to nucleotide sequences that are very common for a particular set of nucleic acid fragments. Primer sequences may be P5 and P7 primers as provided by Illumina, Inc., San Diego, Calif. The primer sequence may also allow a capture probe to bind to a solid support, such as a template particle.

This process may comprise hybridizing the reverse transcription primer to the probe followed by a reverse transcription reaction. The complement of a nucleic acid when aligned need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

Reverse transcription can also be used to add a barcode, a unique molecular identifier (UMI), sequencing adaptors, or any additional sequences of nucleotides to the final cDNA product. For example, the reverse transcription primer may include additional bases that add the barcode or UMI to cDNA product.

A barcode is any sequence of nucleotides which may be used to derive information regarding the nucleic acid product, for example after sequencing. For example, the same sample barcode may be attached to each nucleic acid from a single sample source. The sample barcode may then be used to differentiate nucleic acids derived from different samples after sequencing the nucleic acids and the sample barcode.

UMIs are a type of barcode that may be provided to a sample to make each nucleic acid molecule, together with its barcode, unique, or nearly unique. This may be accomplished by adding one or more UMIs to one or more capture probes of the present invention. By selecting an appropriate number of UMIs, every nucleic acid molecule in the sample, together with its UMI, will be unique or nearly unique.

UMIs are advantageous in that they can be used to correct for errors created during amplification, such as amplification bias or incorrect base pairing during amplification. For example, when using UMIs, because every nucleic acid molecule in a sample together with its UMI or UMIs is unique or nearly unique, after amplification and sequencing, molecules with identical sequences may be considered to refer to the same starting nucleic acid molecule, thereby reducing amplification bias. Methods for error correction using UMIs are described in Karlsson et al., 2016, "Counting Molecules in cell-free DNA and single cells RNA", Karolinska Institute, Stockholm Sweden, incorporated herein by reference.

For example, in the context of RNA analysis, it may be advantageous to analyze the relative or absolute amounts of each RNA molecule in a sample, for example a single-cell sample. Typical methods of RNA analysis, however, first require reverse transcription of the RNA molecules into cDNA copies, followed by amplification of the cDNA molecules. The cDNA molecules must then be amplified in order to create sufficient nucleic acids to be analyzed. As a result, the absolute number of each original RNA molecule present in the sample is lost, with multiple copies of each molecule now present in the prepped sample to be analyzed. Moreover, due to amplification bias that results in the non-uniform amplification of some cDNA molecules at a greater degree than other cDNA molecules, information regarding the relative amounts of each RNA molecule in the original sample is also lost. By providing a UMI to each cDNA molecule prior to amplification, each cDNA molecule (corresponding to each RNA molecule in the sample) is made unique or nearly unique. After amplifying each cDNA molecule (together with its UMI), the amplified cDNA molecules can then be sequenced, and sequence reads generated for each molecule. Sequence reads having both the same base sequence and UMI can be collapsed into a single sequence read and considered a read from a single RNA molecule in the original sample. Sequence reads having the same base sequence but different UMIs are not collapsed, and each sequence read is considered a separate instance of the RNA molecule present in the original sample.

After reverse transcription, biotinylated capture baits or probes may also be used for the targeted enrichment of specific cDNA molecules of interest. Biotinylated capture probes may comprise RNA, DNA, or a hybrid of RNA and DNA nucleotides. The biotinylated RNA capture probes may be added to the cDNA library and incubated for a period of time and at a temperature sufficient for the biotinylated RNA capture probes to hybridize to their target molecules of cDNA based on Watson-Crick base pairing. For example, the mixture containing cDNA and probes may be incubated at 65 degrees Celsius for 24 hours. After hybridization, the biotinylated RNA capture probes that are hybridized with the target cDNA molecules may be captured and segregated using streptavidin or an antibody. The target cDNA molecules can then be amplified and sequenced.

Any known sequencing technology may be used to analyze cDNA reverse transcribed by reverse transcriptases and methods of the invention. An example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured, and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference. For example, an Illumina Mi-Seq sequencer may be used to generate a plurality of sequence reads that may be uploaded to a web portal for analysis by, for example, the Genome Analysis Toolkit (GATK) and/or analyzed using methods shown in U.S. Pat. No. 8,209,130, incorporated by reference.

Analyzing the sequence reads may be performed using known software and following a multistep procedure known in the art. For example, first, the quality of each sequence read, i.e., FASTQ sequence, may be assessed using the software FASTQC. Next, the reads may be trimmed by, for example, Trimmomatic software. The trimmed sequence reads may then be mapped to a human genome using the HISAT2 software. HISAT2 output files in a SAM (sequence alignment/map format), which may be compressed to binary sequence alignment/map files using SAMtools version prior sequence read quantification. Afterward, mapped reads may be counted using the feature Counts software.

Reverse Transcriptases

As discussed above, a reverse transcriptase is an enzyme used to generate cDNA from an RNA template, a process termed reverse transcription. It is mainly associated with retroviruses. However, some non-retroviruses also use reverse transcriptase. Retroviral reverse transcription has three sequential biochemical activities: RNA-dependent DNA polymerase activity, ribonuclease H, and DNA-dependent DNA polymerase activity. These activities are used by the retrovirus to convert single-stranded genomic RNA into double-stranded cDNA. The same sequence of reactions is used in the laboratory to convert RNA to cDNA for use in molecular cloning, RNA sequencing, polymerase chain reaction, or genome analysis.

Reverse transcriptases are members of a specific enzymatic family included in the DNA polymerase superfamily. Enzymes of this superfamily, despite a relatively low amino acid sequence homology and distinct origin, share a similar 3D structure, where DNA polymerase consists of 3 separate domains: palm, thumb, and fingers. In addition, reverse transcriptases with RNAse H activity reveal the unique RNAse H domain with a respective active site and connection domain.

The Moloney murine leukemia virus (MMLV) is a retrovirus known to cause cancer in mice, and its associated reverse transcriptase may be used in the laboratory to convert RNA to cDNA. The MMLV wild type reverse transcriptase is a 75-kDa monomer that has optimal activity at 37° C. (approximately the median body temperature of a mouse or a human). The MMLV reverse transcriptase comprises domains referred to as fingers, palm, thumb, connection, and RNase H domains. The active site of the DNA polymerase reaction resides in the fingers/palm/thumb domain, while that of RNase H reaction lies in the RNase H domain.

Fingers (41-124, 160-192 a.a.), palm (1-40, 125-159, 193-275 a.a.), and thumb (276-361) domains comprise the N-terminal of MMLV RT, while connection domain (362-496 a.a.) and RNAse H (497-671 a.a.) are located at the C-terminal part. Fingers domain has been proposed to provide an intermediate binding site for template-primer in between phosphonucleotidyl transfer reactions. The thumb domain plays a crucial role in substrate binding and processivity. In the palm domain, regions I125-F155, L220-E233, and K257-E275 are located on the surface, interacting with a template. The connection domain comprises P360-K373, Y394-A436, and S453-A462 on the surface, which interacts with a template, and five consecutive hydrophobic residues L432-V433-I434-L435-A436. RNAse H domain can change its conformation and is believed to participate in the processive DNA synthesis.

The Superscript II reverse transcriptase (ThermoFisher) is a mutant MMLV reverse transcriptase that has reduced RNase H activity and increased thermal stability as compared to the wild type MMLV reverse transcriptase. The Superscript II reverse transcriptase is a commonly-used commercial form of the enzyme and is the primary basis below for comparison of reverse transcriptases of the invention. The sequence of the Superscript II reverse transcriptase is shown in SEQ ID NO: 2.

A reverse transcriptase of the invention has at least one amino acid substitution as compared to the reverse transcriptase of SEQ ID NO: 2.

Modified reverse transcriptases of the invention have increased thermal stability with respect to both the wild type version and the Superscript II version of the enzyme. Increased thermal stability of one reverse transcriptase relative to another reverse transcriptase means that the reverse transcriptase with increased thermal stability is less prone to loss of activity at elevated temperatures, for example, above 37° C. Increased stability of an enzyme also may include avoidance of denaturation mechanisms in order to realize their full potential as catalysts. Moreover, for cDNA synthesis, a higher reaction temperature is desirable because it reduces RNA secondary structures and nonspecific primer binding. Stability between two enzymes can be determined by comparing the remaining activity of both enzymes after exposure to a particular condition (for example, elevated temperature, in the presence of inhibitors of that enzyme, or in fixed samples). Alternatively, the stability may be determined by comparing the remaining or residual acidity of the enzyme after incubation at a given condition (for example time or temperature) as compared to the initial activity before incubation.

Increased efficiency of one reverse transcriptase relative to another reverse transcriptase means that under a set of conditions, the more efficient enzyme results in fewer base calling errors over time.

Increased activity of one enzyme relative to another enzyme means that the enzyme with increased activity converts the substrate at a higher rate—with regard to reverse transcription, this means the rate at which RNA (the substrate) is used to synthesize cDNA. The SI unit for enzyme activity is katal (1 katal=1 μmol s$^{-1}$). A more practical and commonly used value is enzyme unit (U)=1 μmol min$^{-1}$. 1 U corresponds to 16.67 nanokatals and is defined as the amount of the enzyme that catalyzes the conversion of 1 micro mole of substrate per minute. The specific activity of an enzyme is the activity of an enzyme per milligram of total protein (expressed in μmol min$^{-1}$mg$^{-1}$).

Reverse transcriptase activity may be determined in an assay measuring formation of cDNA over time. For example, a reverse transcriptase may be incubated with an RNA template, primers and a suitable dNTP mixture, and the production of cDNA or consumption of dNTP may be monitored.

Disclosed herein are reverse transcriptases that comprise amino acid substitutions of at least one amino acid substitution at an amino acid position selected from positions 56, 138, 234, 290, 344, 420, 424, 444, 615, 444, 615, 642, 524, 583, 562, 204, and 306 with respect to SEQ ID NO: 2. For example, the amino acid substitutions may be:

S at position 56 substituted with G, A, V, L, or I;
G at position 138 substituted with S, C, T, or M;
S at position 232 substituted with C, T, or M;
L at position 234 substituted with D, E, N, Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I;
D at position 615 substituted with E, N, or Q;
H at position 642 substituted with D, E, N, or Q.
D at position 524 substituted with G, A V, L, or I;
D at position 583 substituted with E, N, or Q;
E at position 562 substituted with D, N, or Q;
H at position 204 substituted with K or R; and
T at position 306 substituted with H, K, or R.

It is understood that the reverse transcriptases of the invention may comprise additional mutations that do not alter the function, i.e. increased thermostability, of the reverse transcriptase.

For example, the reverse transcriptase may comprise additional conservative mutations. Conservative amino acid substitutions are substitutions of an amino acid with a different amino acid having similar properties, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

In aspects of the invention, the reverse transcriptase does not comprise one or more of following mutations: E5K; M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; L671P, A32V, E286R, E302K, W388R, and L435R. For example, the reverse transcriptase comprises the wild type amino acid at the positions identified, or a conservative substitution at the wild type amino acid position.

A reverse transcriptase with at least X% sequence identity means that the enzyme has an amino acid sequence characterized in that, within a stretch of 100 amino acids, at least X amino acids residues are identical to the sequence of the corresponding sequence. Sequence identity may be determined by sequence alignment in the form of sequence comparison. Methods of sequence alignment are well known in the art and include various programs and alignment algorithms. The Basic Local Alignment Search Tool (BLAST) may also be used in connection with the sequence analysis programs blastp, blastn, blastx, tblastn and tblastx.

For example, because the wild type MMLV is 671 amino acids in length, the enzyme may tolerate a number of substitutions, for example conservative substitutions, without losing the reverse transcription properties of the enzyme. However, it is understood that mutations at certain positions relative to the wild type will reduce efficacy of the wild type enzyme, while other rarer substitutions may increase efficacy of the wild type enzyme. Accordingly, by the present invention, it has been discovered that amino acid substitutions at amino acid positions 56, 72, 138, 163, 234, 249, 290, 344, 420, 424, 444, 615, 444, 615, 642, 524, 583, 562, 204, and 306 may enhance the properties of the wild type enzyme. It is understood that an enzyme comprising substitutions at each of the 20 positions identified by present invention would have a 97.32% sequence identity with the wild type enzyme. Enzymes of the present invention may comprise additional substitutions that do not alter the properties of the present invention, for example an additional 15 amino acid substitutions, for example conservative substitutions. Accordingly, the enzyme of the present invention may have 95% sequence identity with the wild type MMLV enzyme. The same principles hold true for the Superscript II version.

Aspects of the invention provide modified reverse transcriptases comprising at least one mutation in at least one domain of the Moloney Murine Leukemia Virus (MMLV) reverse transcriptase of SEQ ID NO: 2. Importantly, modified reverse transcriptases of the invention exhibit increased thermal stability relative to the wild type reverse transcriptase such that at temperatures of about 50° C. or greater the activity is at least about 90% of the activity of the wild type reverse transcriptase at 42° C.

Preferred amino acid substitutions occur at positions 27, 138, 200, 204, 212, 218, 231, 232, 234, 237, 242, 249, 264, 265, 267, and/or 272 in a palm domain of the MMLV reverse transcriptase, positions 43, 46, 48, 54, 56, 72, 163, and/or 177 in a finger domain of the MMLV reverse transcriptase, positions 280, 281, 290, 306, 335, 338, 339, 344, 345, 346, and/or 349 in a thumb domain of the MMLV reverse transcriptase, positions 376, 413, 420, 424, 443, and 444 in a connection domain of the MMLV reverse transcriptase, and positions 518, 524, 528, 550, 554, 562, 583, 615, 619, 625, 629, 642, and/or 658 in the RNAse H domain of the MMLV reverse transcriptase.

Preferred substitutions are selected from:
S at position 56 substituted with G, A, V, L, or I;
L at position 72 substituted with Q or R;
G at position 138 substituted with S, C, T, or M;
H at position 204 substituted with K or R;
S at position 232 substituted with C, T, or M;
L at position 234 substituted with D, E, N, Q;
G at position 290 substituted with H, K, or R;
T at position 306 substituted with H, K, or R
Y at position 344 substituted with F or M;
T at position 420 substituted with G, A, V, L, or I;
G at position 424 substituted with D, E, N, or Q;
V at position 444 substituted with G, A, L, or I;
D at position 524 substituted with G, A V, L, or I;
E at position 562 substituted with D, N, or Q;
D at position 583 substituted with E, N, or Q;
D at position 615 substituted with E, N, or Q; and
H at position 642 substituted with D, E, N, or Q.

In addition, modified reverse transcriptases may have substitutions in at least one to at least 14 amino acid positions selected from positions 56, 72, 138, 204, 232, 234, 290, 306, 344, 420, 424, 444, 524, 562, 583, 615, and 642.

In some embodiments, the amino acid substitution is selected from S56A, G138S, S232T, L234E, G290K, Y344F, T420V, G424D, V444I, and D615E. The modified enzyme may comprise an additional substitution selected from G524D, N583D, and Q562E. In other embodiments, the amino acid substitution is selected from L72Q, T163K, N249E, and H642D. In still other embodiments, the amino acid substitution is selected from S56A, G138S, S232T, L234E, G290K, Y344F, T420V, G424D, V444I, D615E, and H642D. This embodiment may also include at least one additional amino acid substitution selected from D524G, D583N, E562Q, H204R, and T306K.

In specific embodiments, the amino acid substitutions may be selected from S27T, V43K, A46P, L48I, A54P, S56A, L72Q, G138S, T163K, M177R, D200H, I212T, I218T, T231E, S232T, L234E, Q237E, A242D, N249E, Q265E, K264Q, K267T, L272I T281S, G290K, N335Q P338E, D339E, Y344F, Q345D E346D, Q349R, Y376F, V413I, T420V, G424D, A442S, V433T, V444I, D518E, G524D, L528F, A554P, E562Q, D583N, K550S, D615E, A619E, F625W/H, R629K, H642D, and K658E.

Modified reverse transcriptases of the invention generally have activity at temperatures of 65° C. or greater that is at least about 50% of the reverse transcription activity of the reverse transcriptase of SEQ ID NO: 2 at about 42° C. Preferably, the activity of the reverse transcriptase is improved compared to the reverse transcriptase of SEQ ID NO: 2 in the presence of inhibitors of reverse transcription. Additionally, modified reverse transcriptases of the invention exhibit increased thermal stability relative to, for example, a reverse transcriptase of SEQ ID NO: 2 and may include at least one amino acid substitution selected from the group consisting of E5K; M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P. Samples and Sample Preparation Any sample suspected of containing one or more nucleic acids that are to be detected or measured and quantified may be analyzed using the reverse transcriptases of the invention. For example, the sample may be a biopsy, a culture, or an environmental sample such as water or soil. Samples may be from a subject, such as an animal or human, they may be fluid, solid, a suspension, or tissue.

Examples of samples include cell or tissue cultures, blood, blood serum, blood plasma, needle aspirate, urine, semen, seminal fluid, seminal plasma, prostatic fluid, excreta, tears, saliva, sweat, biopsy, ascites, cerebrospinal fluid, pleural fluid, amniotic fluid, peritoneal fluid, interstitial fluid, sputum, milk, lymph, bronchial and other lavage samples, or tissue extract samples. The source of the sample may be solid tissue as from a fresh, frozen and/or preserved organ or tissue sample or biopsy or aspirate; or cells from any time in gestation or development of the subject. In a preferred embodiment of the method, the sample is selected from the group consisting of a body fluid, blood, blood plasma, blood serum, urine, bile, cerebrospinal fluid, a swab, a clinical specimen, an organ sample and a tissue sample, particularly a human, an animal or a plant, especially a human.

The sample may contain compounds which are naturally intermixed in nature as well as compounds not naturally intermixed with the sample in nature such as preservatives, anticoagulants, buffers, fixatives, nutrients, antibiotics, or the like.

Notably, many samples contain both natural and non-natural inhibitors of reverse transcriptases. For example, humic/fulvic acid, polysaccharides, phenolics, and flavonoids in plant samples inhibit reverse transcription activity. Additionally, proteins and fats from tissue samples, bile salts from stool samples, collogen from connective tissue samples, melanin and eumelanin in hair and skin samples, myoglobin from muscle tissue samples, complex polysaccharides in fecal samples, proteinases and calcium ions in milk and bone samples, and urea in urine samples all inhibit transcriptase activity. In addition, heme, hemoglobin, lactoferrin, and antibodies in blood samples all inhibit transcription activity.

Sample preparation steps also frequently introduce products that inhibit reverse transcriptases, for example EDTA, detergents/DDT, alcohols, salts, heparin, hematin, phenol: chloroform, proteases, nucleases, agarose, metal ions, and aldehydes all inhibit reverse transcription activity. Moreover, some artificial sample preparation products are introduced into a sample for the very purpose of removing unwanted natural products in the sample. For example, ethanols, proteinases, and phenol: chloroforms are typically used to wash samples of excess proteins, salts, and other natural products, and yet are themselves transcriptase inhibitors. Other sample preparation products are necessary for analysis of sample types. For example, detergents are frequently introduced to samples comprising cells in order to cause cell lysis and release nucleic acids to be analyzed. Detergents are also frequently used in methods of single cell sequences, for example droplet sequencing, to separate and compartmentalize individual cells for sequencing.

As a consequence, samples are typically washed of unwanted products or no-longer needed reagents multiple times during sample preparation. However, each washing results in the loss of at least some of the original sample and risks the introduction of contaminants.

Sample preservation steps may also result in the introduction of reverse transcriptase inhibitors. For example, Formalin-Fixed Paraffin-Embedded (FFPE) tissue preservation methods are a form of preservation and preparation for biopsy specimens. The tissue sample is first preserved by fixing it in formaldehyde to preserve the proteins and vital structures within the tissue. Next, it is embedded in a paraffin wax block, which allows for ease of cutting slices of required sizes to mount on a microscopic slide for examination. However, FFPE sample preparation also results in inhibition of reverse transcription activity.

Reverse transcriptases of the present invention exhibit improved reverse transcriptase activity in the presence of inhibitors of reverse transcriptase and preserved samples, for example FFPE samples, as compared to either the wild type MMLV enzyme or the reverse transcriptase shown in SEQ ID NO: 2. As a result, reverse transcriptases of the invention may be added directly to samples comprising an inhibitor without additional washing steps that result in the loss of the original sample or the introduction of contaminants. Additionally, reverse transcriptases of the invention may be added directly to preserved samples, for example fixed samples, also without the loss of reverse transcriptase activity.

Specifically, reverse transcriptases of the invention demonstrate improved activity in the presence of inhibitors of reverse transcription relative to the reverse transcriptase of SEQ ID NO: 2 and may include at least one amino acid substitution selected from the group consisting of M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

In other embodiments, the activity of the reverse transcriptase is improved in formalin-fixed samples relative to the reverse transcriptase of SEQ ID NO: 2 and may include at least one amino acid substitution selected from the group consisting of M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

In still other embodiments, a reverse transcriptase of the invention exhibits increased thermal stability relative to the reverse transcriptase of SEQ ID NO: 2 and may include at least one amino acid substitution selected from the group consisting of A32V, E286R, E302K, W388R, and L435R.

The activity of reverse transcriptases of the invention is also improved in the presence of inhibitors of reverse transcription relative to the reverse transcriptase of SEQ ID NO: 2 and may include at least one amino acid substitution selected from the group consisting of A32V, E286R, E302K, W388R, and L435R. Likewise, the activity of reverse transcriptases of the invention is improved for formalin-fixed samples relative to the reverse transcriptase of SEQ ID NO: 2 and may include at least one amino acid substitution selected from the group consisting of A32V, E286R, E302K, W388R, and L435R.

Preferred reverse transcriptases of the invention comprise a at least about 95% sequence identity with respect to the reverse transcriptase of SEQ ID NO: 2.

Aspects of the invention include methods of reverse transcribing cDNA from RNA. Preferred methods include providing to a sample comprising RNA a modified reverse transcriptase of the invention comprising at least one mutation in at least one domain of the reverse transcriptase of SEQ ID NO: 2, wherein the modified reverse transcriptase exhibits an increased thermal stability relative to the thereto, such that an activity of the reverse transcriptase at temperatures of about 50° C. or greater is at least about 90% of the activity of the reverse transcriptase of SEQ ID NO: 2 at 37° C., and providing to the sample reagents for reverse transcription, and performing a reverse transcription reaction between the reverse transcriptase and the RNA in the sample. The reverse transcription reaction is conducted at a temperature of 50° C. or greater to form the cDNA.

In certain embodiments, the mutation comprises an amino acid substitution at a position selected from positions 27, 138, 200, 204, 212, 218, 231, 232, 234, 237, 242, 249, 264, 265, 267, and 272 in a palm domain of the reverse transcriptase, positions 43, 46, 48, 54, 56, 72, 163, and 177 in a finger domain of the reverse transcriptase, positions 280, 281, 290, 306, 335, 338, 339, 344, 345, 346, and 349 in a thumb domain of the reverse transcriptase, positions 376, 413, 420, 424, 443, and 444 in a connection domain of the reverse transcriptase, and positions 518, 524, 528, 550, 554, 562, 583, 615, 619, 625, 629, 642, and 658 in the RNAse H domain of the reverse transcriptase.

For example, the amino acid substitution may be selected from:
S at position 56 substituted with G, A, V, L, or I;
L at position 72 substituted with Q or R;
G at position 138 substituted with S, C, T, or M;
H at position 204 substituted with K or R;
S at position 232 substituted with C, T, or M;
L at position 234 substituted with D, E, N, Q;
G at position 290 substituted with H, K, or R;
T at position 306 substituted with H, K, or R
Y at position 344 substituted with F or M;
T at position 420 substituted with G, A, V, L, or I;
G at position 424 substituted with D, E, N, or Q;
V at position 444 substituted with G, A, L, or I;
D at position 524 substituted with G, A V, L, or I;
E at position 562 substituted with D, N, or Q;
D at position 583 substituted with E, N, or Q;
D at position 615 substituted with E, N, or Q; and
H at position 642 substituted with D, E, N, or Q.

The modified reverse transcriptases may comprise substitutions in at least 3 amino acid positions and up to at least 12 amino acid positions, wherein the amino acid positions are selected from positions 56, 72, 138, 204, 232, 234, 290, 306, 344, 420, 424, 444, 524, 562, 583, 615, and 642. Specifically, the at least one amino acid substitution may be selected from S56A, G138S, S232T, L234E, G290K, Y344F, T420V, G424D, V444I, and D615E. In certain embodiments, the modified reverse transcriptases comprise at least one additional amino acid substitution selected from G524D, N583D, and Q562E. The amino acid substitution is selected from L72Q, T163K, N249E, and H642D. Additionally and/or alternatively, the amino acid substitution is selected from S56A, G138S, S232T, L234E, G290K, Y344F, T420V, G424D, V444I, D615E, and H642D. This embodiment may further comprise at least one additional amino acid substitution selected from D524G, D583N, E562Q, H204R, and T306K.

Generally, the activity of the reverse transcriptases at temperatures of about 65° C. or greater is at least about 50% of the reverse transcription activity of the reverse transcriptase of SEQ ID NO: 2 at about 42° C.

Additionally, in methods of the invention, the sample comprising RNA may comprise one or more inhibitors of reverse transcription and the reverse transcription reaction may be more efficient than a reverse transcription reaction conducted using the reverse transcriptase of SEQ ID NO: 2 in the presence of the one or more. The sample comprising RNA may be formalin fixed, and the reverse transcription reaction may be more efficient than a reverse transcription reaction conducted with the reverse transcriptase of SEQ ID NO: 2 on a formalin-fixed sample.

In further embodiments, the performing step is conducted at a temperature of about 65° C. or greater and wherein the reverse transcription reaction is at least about 50% as active as a reverse transcription reaction conducted using the reverse transcriptase of SEQ ID NO: 2 at about 42° C.

Methods of the invention may further comprise any known reagents and methods for reverse transcription. For example, the providing step may comprise providing to the sample capture oligos that capture target RNA molecules.

EXAMPLES

Data are given characterizing RT enzymes of the disclosure.

FIG. 1A gives qPCR results showing that prod-ana RT has competitive thermo-activity with Maxima in RT-qPCR.

FIG. 1B gives efficiency scores for the enzymes.

First strand synthesis (FSS) was run at 50° C. and 60° C. using 10, 1, and 0.1 ng of total liver RNA as input with RT enzymes of the disclosure and Maxima followed by qPCR.

First strand synthesis (FSS) reactions were generated on ice by mixing 10 ng of total liver RNA, 1X reaction buffer (50 mM Tris-HCl pH 8.3, 75 mM KCl, 3 mM $MgCl_2$), 10U Murine RNase Inhibitor, 5 uM oligo-dT(20), 0.5 mM dNTPs, and 200U specified reverse transcriptase. FSS was run at various temperatures (42-65° C.) for 25 minutes followed by qPCR to assess cDNA yield. qPCR reactions were generated by mixing 1X SsoAdvanced Universal SYBR Green Supermix, 10% of the FSS reaction, and 0.6 uM of primers that anneal to the 5' end of the beta-actin gene.

The resulting cDNA values were assessed via Ct values as shown in FIG. 1. cDNA yields from prod-blh FSS are greater than 100-fold lower when FSS is incubated at 50° C. compared to 60° C. whereas prod-ana and Maxima are able to convert similar amounts of RNA to cDNA at 50° C. and 60° C. Prod-ana has competitive or better yields and efficiency than Maxima RNaseH minus reverse transcriptase at 50° C. and 60° C.

Figure 1C:
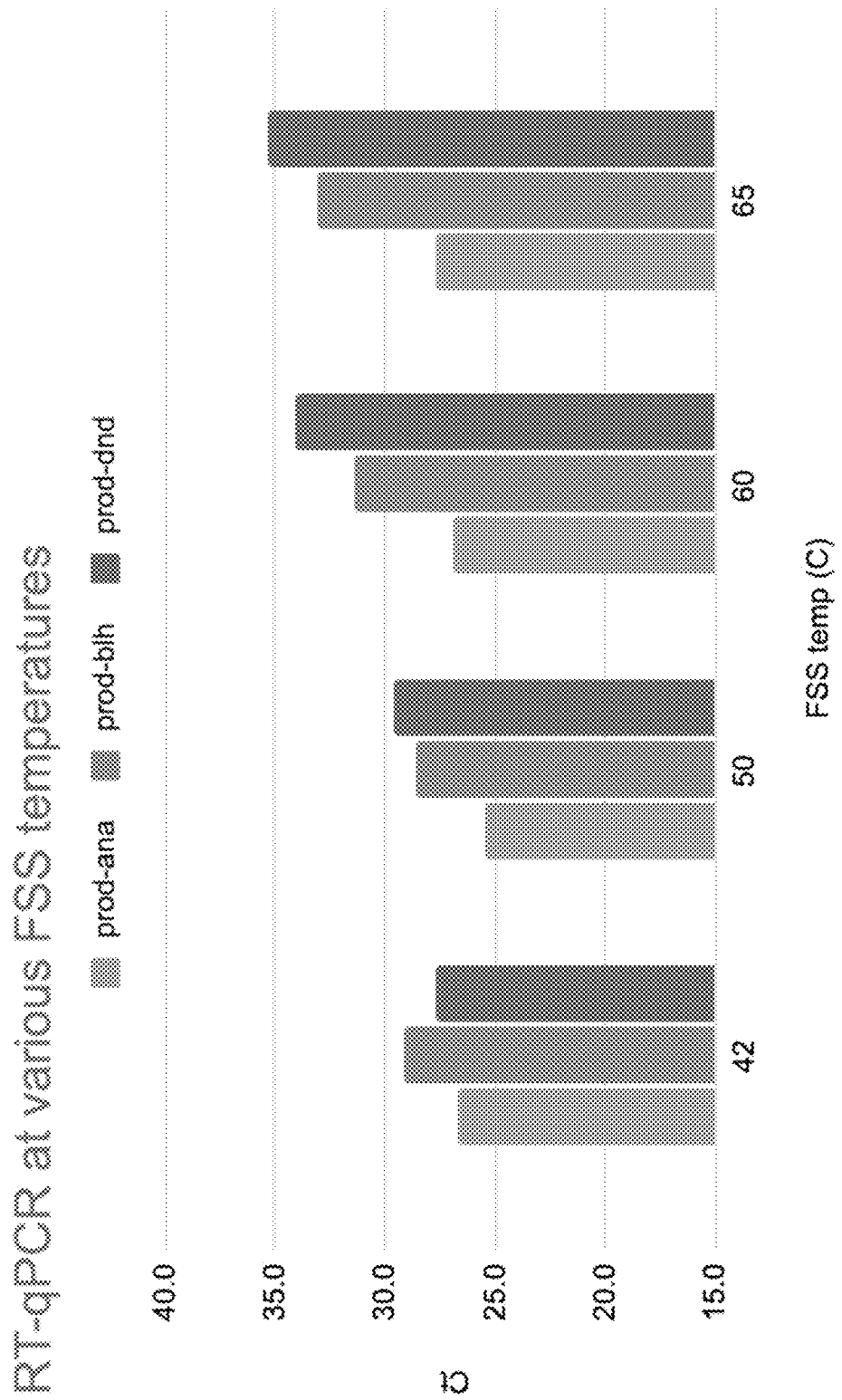
FIG. 1C shows RT-qPCR yields at elevated using RT enzymes of the disclosure.

FIG. 1C shows RT-qPCR yields at elevated using RT enzymes of the disclosure. First strand synthesis (FSS) reactions were generated on ice by mixing 10 ng of total liver RNA, 1X reaction buffer (50 mM Tris-HCl pH 8.3, 75 mM KCl, 3 mM $MgCl_2$), 10U Murine RNase Inhibitor, 5 uM oligo-dT(20), 0.5 mM dNTPs, and 200U specified reverse transcriptase. FSS was run at various temperatures (42-65° C.) for 25 minutes followed by qPCR to assess cDNA yield. qPCR reactions were generated by mixing 1X SsoAdvanced Universal SYBR Green Supermix, 10% of the FSS reaction, and 0.6 uM of a primers that anneal to the 5' end of a Beta-actin gene.

The resulting cDNA values were assessed via Ct values and are shown in FIG. 1C. Prod-blh had equivalent cDNA yield at 42° C. and 50° C. Prod-ana was the most thermostable variant and had equivalent yields at all temperatures tested.

Figure 2A:
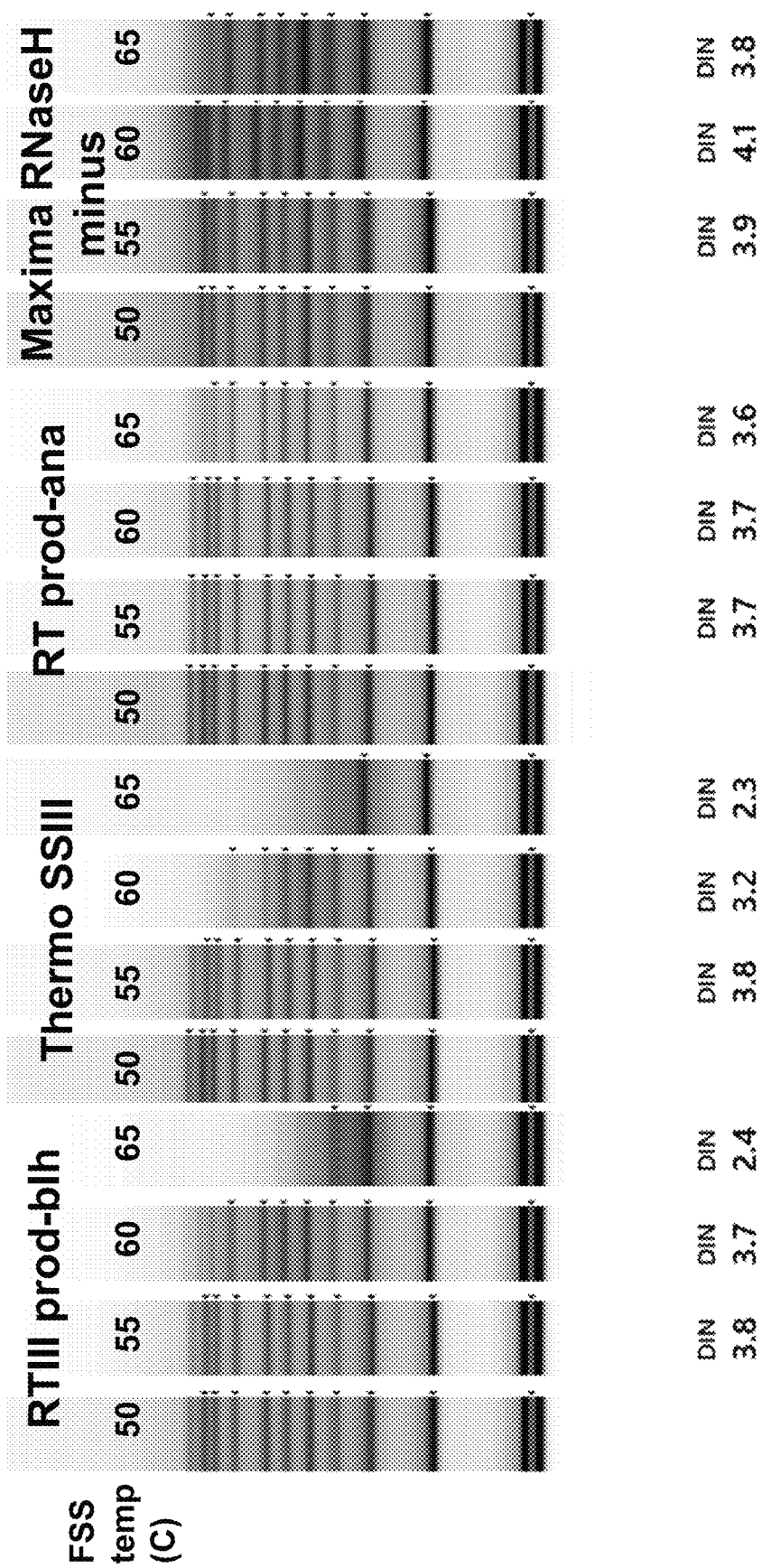
FIG. 2A shows enhanced thermo-activity of RT enzymes of the disclosure.

FIG. 2A shows RT prod-ana has enhanced thermo-activity. In an RNA ladder assay, 10 polyA RNA transcripts from 0.5 kb to 9 kb are used as RNA input into first strand synthesis (FSS). Specifically, FSS reactions were generated on ice by mixing 500ng of Millennium RNA ladder (Millennium™ RNA Markers), 1X reaction buffer (50 mM Tris-HCl pH 8.3, 75 mM KCl, 3 mM $MgCl_2$), 10U Murine RNase Inhibitor, 5 uM oligo-dT(20), 0.5 mM dNTPs, and 200U specified reverse transcriptase. FSS was run at various temperatures (42-65° C.) and thermostability and processivity of the RT variants were analyzed on an electrophoresis tool (e.g., gDNA TAPESTATION instrument, Agilent). For example, prod-blh, prod-ana, Thermo SSIII, and Thermo Maxima RNaseH minus were run in the RNA ladder assay wherein FSS was employed at 50, 55, 60 or 65° C. for 30 minutes. Processivity of the reverse transcriptases was assessed qualitatively by the conversion, or lack thereof, of the higher MW RNA transcripts to cDNA.

The gDNA tapestation and resulting cDNA products from the RNA ladder assay is shown in FIG. 2A. Transcript length at various temperatures aligns with thermostability of the enzymes. Prod-blh converts the entire RNA ladder to cDNA when FSS temperature is performed at 42° C. or 50° C. When FSS temperatures are elevated to 60° C. or 65° C. the entire RNA ladder is not converted to cDNA. Prod-blh has very competitive cDNA conversion across all temperatures to Thermo SSIII reverse transcriptase. Prod-ana converts the entire RNA ladder to cDNA when FSS temperature is performed at 42° C., 50° C., or 60° C. When FSS temperatures are elevated to 65° C. the upper MW RNA transcript is not converted to cDNA. Prod-ana has very competitive cDNA conversion across all temperatures to Thermo Maxima RNaseH minus reverse transcriptase. RT prod-ana has enhanced thermostability and processivity compared to SSIII and competitive thermostability and processivity compared to Maxima RNaseH minus. RT variants of the disclosure were run in triplicates in a thermal shift assay to assess enzyme thermostability.

FIG. 2B shows processivity of RT enzymes of embodiments of the disclosure at elevated temperatures.

FSS reactions were generated on ice by mixing 500 ng of Millenium RNA ladder (Millennium™ RNA Markers), 1X reaction buffer (50 mM Tris-HCl pH 8.3, 75 mM KCl, 3 mM $MgCl_2$), 10U Murine RNase Inhibitor, 5 uM oligo-dT(20), 0.5 mM dNTPs, and 200U reverse transcriptase. FSS was run at various temperatures (42-65° C.) and thermostability and processivity of the RT variants were analyzed on a gDNA tapestation. Processivity of the reverse transcriptases was assessed qualitatively by the conversion, or lack thereof, of the higher MW RNA transcripts to cDNA.

The gDNA tapestation and resulting cDNA products from the RNA ladder assay is shown in FIG. 2B. Transcript length at various temperatures aligns with thermostability of the enzymes:
1. There is no cDNA conversion when no RT is present (data not shown)
2. All reverse transcriptases are able to convert all MW RNA transcripts to cDNA at 42° C. and 50° C.
3. At 55° C. Prod-dnd does not fully convert all transcripts of the RNA input to cDNA. Prod-blh, prod-ana, and prod-cnc are able to fully convert all transcripts at 55° C. and 60° C.
4. At 65° C. prod-ana converts 9 of the 10 polyA transcripts to cDNA.

Figure 3A:
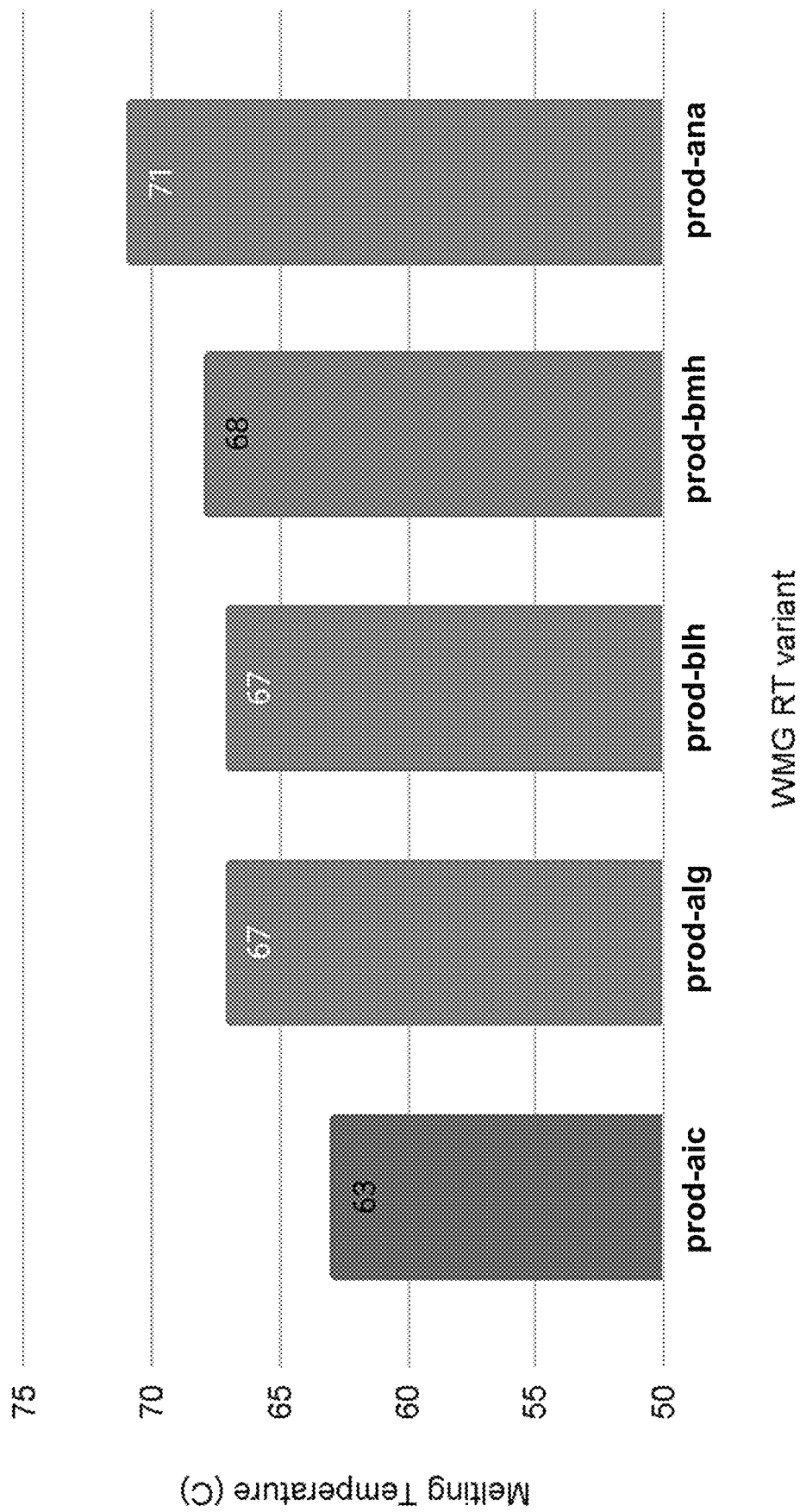
FIG. 3A shows thermostability of RT variant enzymes of the disclosure.

FIG. 3A shows thermostability of RT variants. WMG RT variants were run in triplicates in a thermal shift assay to assess enzyme thermostability. RT variants of the disclosure were run in triplicates in a thermal shift assay (GloMelt; Biotium) to assess enzyme thermostability. Biotium GloMelt manufacturing protocols were followed, and a thermal ramp gradient was employed. As the enzyme unfolds fluorescence signal increases and the inflexion point of the curves indicates the melting temperature for that enzyme.

Figure 3B:
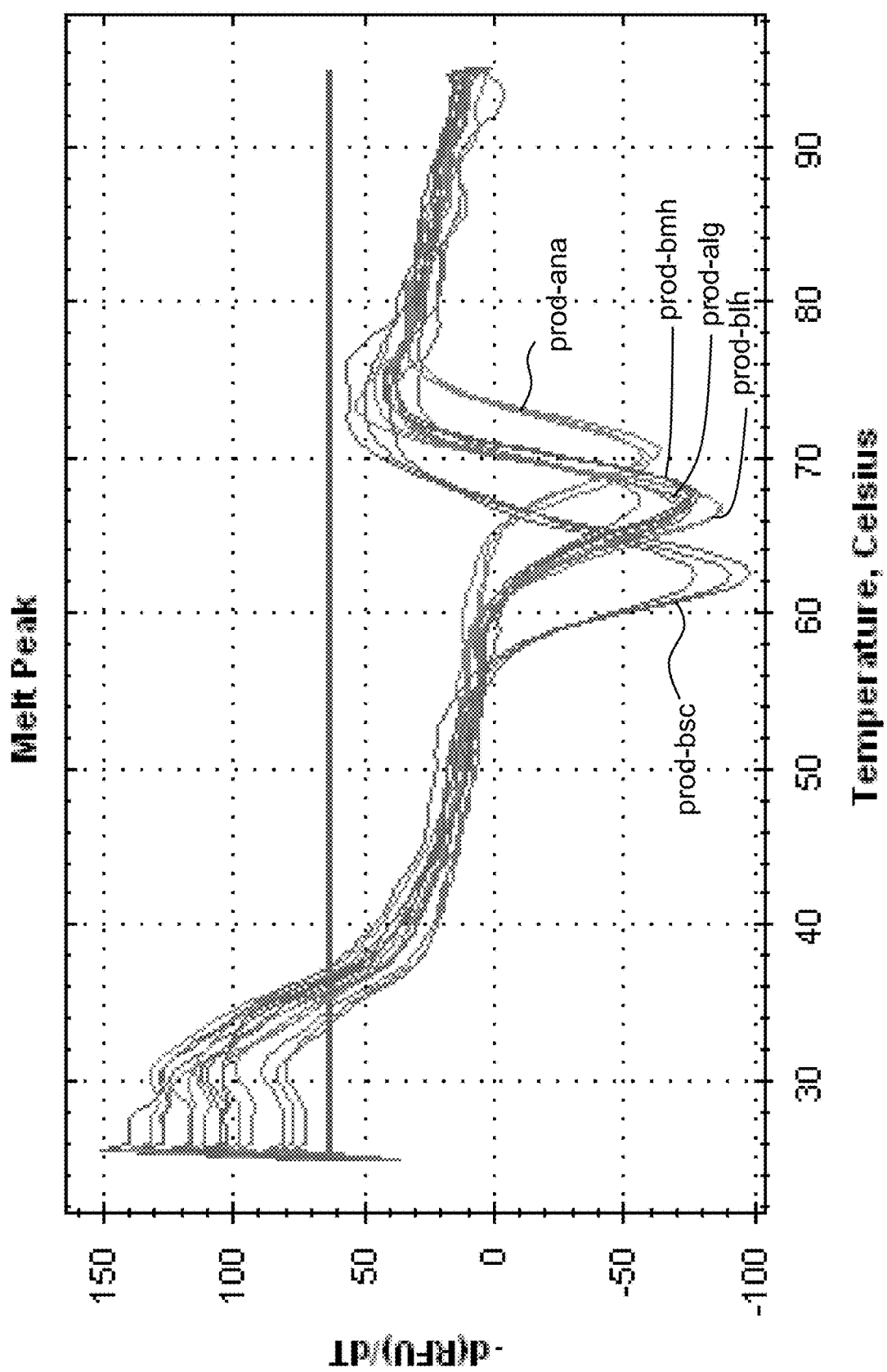
FIG. 3B shows melt curves indicative of thermostability.

FIG. 3B shows a melt curve that indicates that the RTs tested have various degrees of thermostability: RTII<prod-alg=RTIII<prod-bmh<prod-ana. Here, prod-ana exhibits a substantial increase in thermal stability compared to RTII and RTIII. As shown, prod-aic (RTII) exhibits a melt curve at 63° C., prod-alg exhibits a melt curve at 67° C., prod-blh (RTIII) exhibits a melt curve at 67° C., prod-bmh exhibits a melt curve at 68° C. and prod-ana exhibits a melt curve at 71° C. To melt curve indicates that the RTs tested have various degrees of thermostability.

Figure 3C:
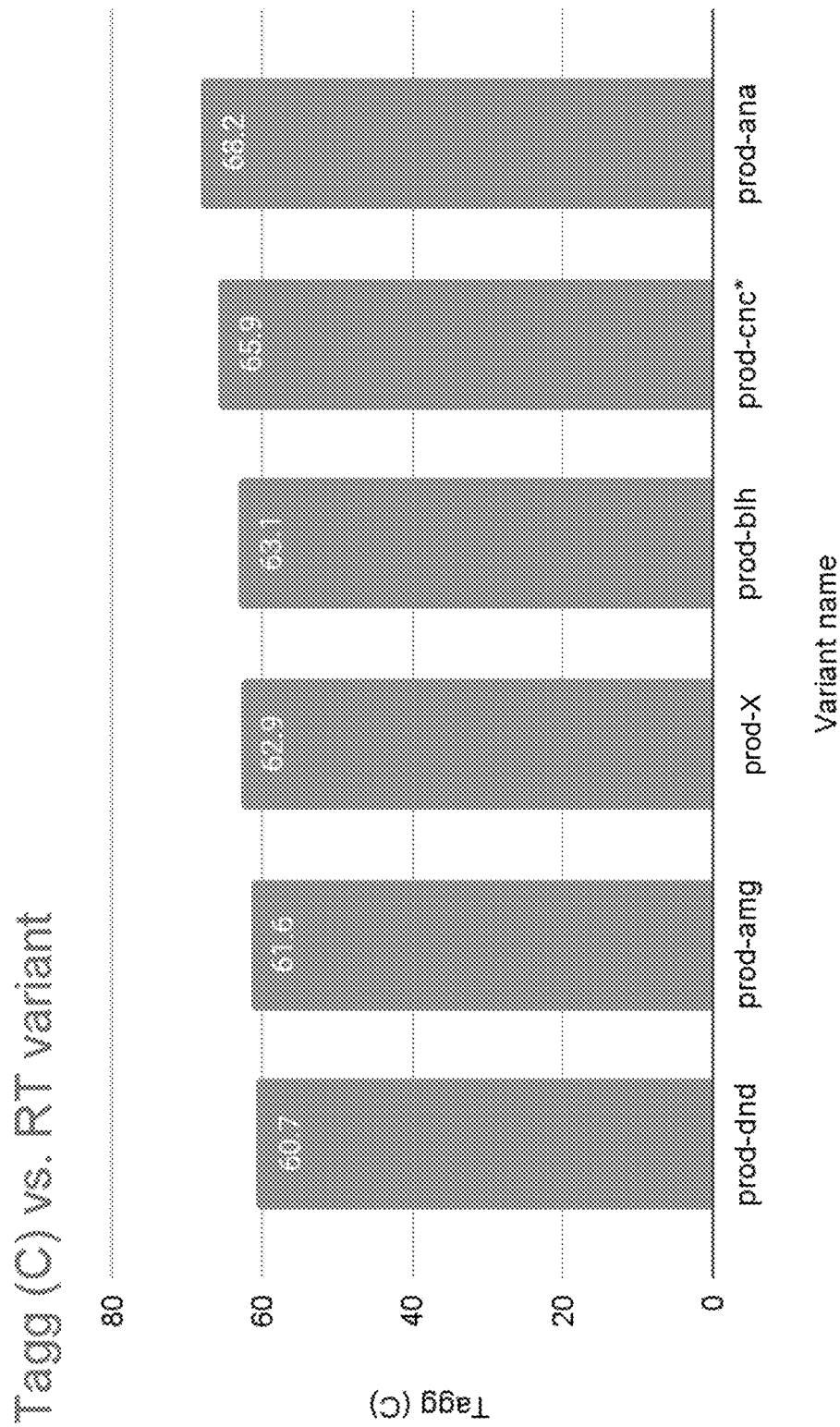
FIG. 3C shows thermal ramp assay results of embodiments of RT enzymes of the disclosure.
Figure 3E:
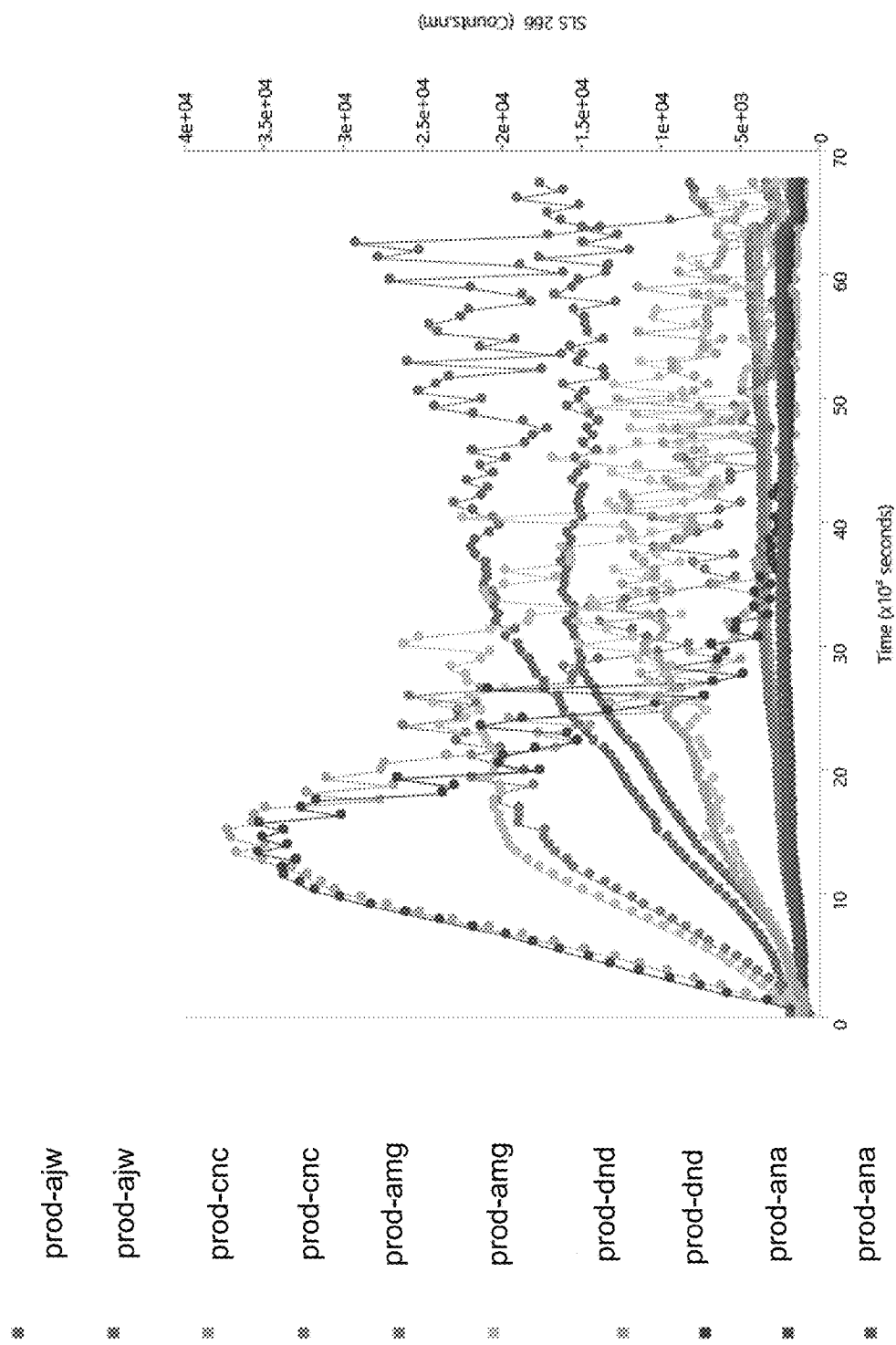
FIG. 3E shows isothermal reaction incubation for embodiments of RT enzymes of the disclosure

FIGS. 3C-3E show the results of further assessment of aggregation temperature and thermostability of reverse transcriptases of the discloser.

FIG. 3C shows thermal ramp assay results of embodiments of RT enzymes of the disclosure. RT variants were run in triplicates on the Unchained Labs Uncle instrument in a thermal ramp assay using static light scattering (SLS) to assess the onset of aggregation. A 266 nm laser was used to monitor the amount of light scattered while a 15° C. to 95° C. thermal ramp was applied to the samples. All RT variants were diluted to 0.25 mg/mL in the following buffer system. 60 mM Tris-HCl (pH=8.0), 75mM KCl, 50mM NaCl, 25% (v/v) Glycerol, 10mM DTT, 3mM $MgCl_2$. An increase in the amount of light scattered directly measures the level of aggregation occurring. Aggregation onset almost always occurs after a melting event occurring within the protein.

FIG. 3D shows a table of results for the thermal ramp assay of FIG. 3C for the RT variants tested. Results:
1. prod-dnd shows the lowest thermal stability with the lowest aggregation onset temperature of 60.7° C.
2. prod-ana shows the highest thermal stability with the highest aggregation onset temperature of 68.2° C.
3. prod-blh shows moderate thermal stability with an aggregation onset temperature between that of prod-dnd and prod-ana at 63.1° C.

FIG. 3E shows isothermal reaction incubation for embodiments of RT enzymes of the disclosure. RT variants were run in triplicates on the Unchained Labs Uncle instrument in an isothermal assay using static light scattering (SLS) to assess the onset of aggregation. A 266 nm laser was used to monitor the amount of light scattered while samples were held at 50° C. for roughly 20 hours. All RT variants were diluted to 0.25 mg/mL in the following buffer system: 60mM Tris-HCl (pH=8.0), 75mM KCl, 50 mM NaCl, 25% (v/v) Glycerol, 10 mM DTT, 3 mM $MgCl_2$. An increase in the amount of light scattered directly measures the level of aggregation occurring. Aggregation rates can be determined by the increase in SLS counts over time.
1. prod-dnd shows the lowest thermal stability with the steepest aggregation rate.
2. prod-ana shows the highest thermal stability with the most horizontal aggregation rate.
3. prod-blh shows moderate thermal stability with an aggregation rate between that of prod-dnd and prod-ana.

RT-qPCR Yields in the Presence of Various Inhibitors

First strand synthesis (FSS) reactions were generated on ice by mixing 10 ng of total liver RNA, 1X reaction buffer (50 mM Tris-HCl pH 8.3, 75 mM KCl, 3 mM $MgCl_2$), 10U Murine RNase Inhibitor, 5 uM oligo-dT(20), 0.5 mM dNTPs, 200 U specified reverse transcriptase in the +/− various inhibitors (see below). FSS was run at temperatures optimal for the various reverse transcriptases, 42° C. for prod-dnd or 50° C. for prod-blh and incubated for 25 minutes followed by qPCR to assess cDNA yield. qPCR reactions were generated by mixing 1X SsoAdvanced Universal SYBR Green Supermix, 10% of the FSS reaction, and 0.6 uM of primers that anneal to the 5' end of the beta-actin gene.

Figure 4A:
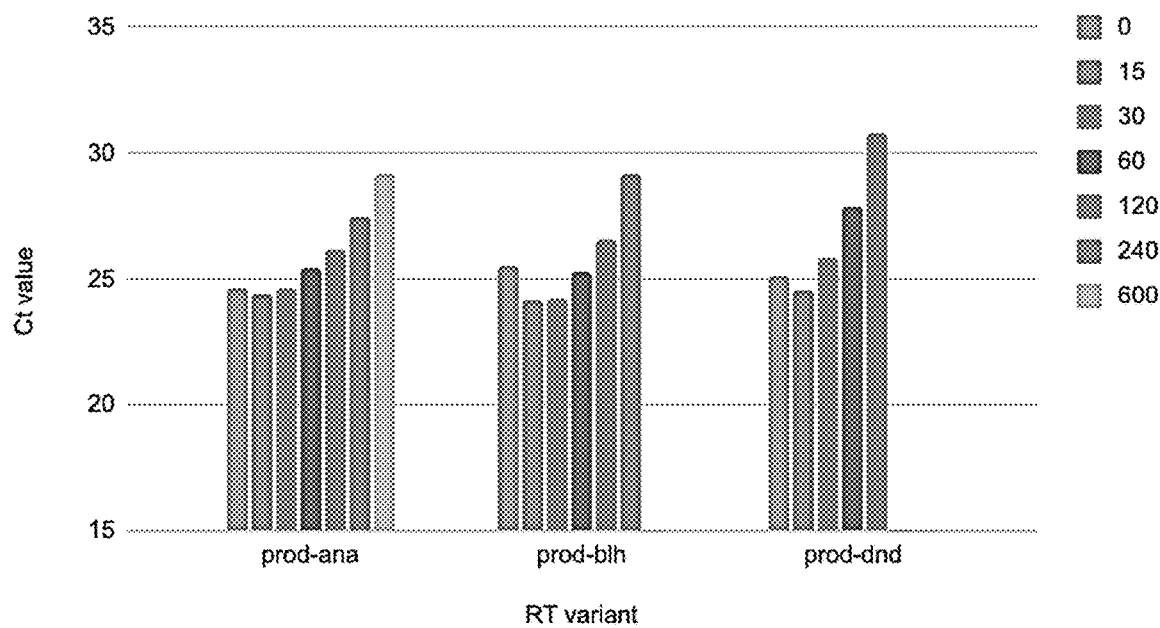
FIG. 4A shows tolerance to inhibition by heparin of embodiments of RT enzymes of the disclosure.
Figure 4B:
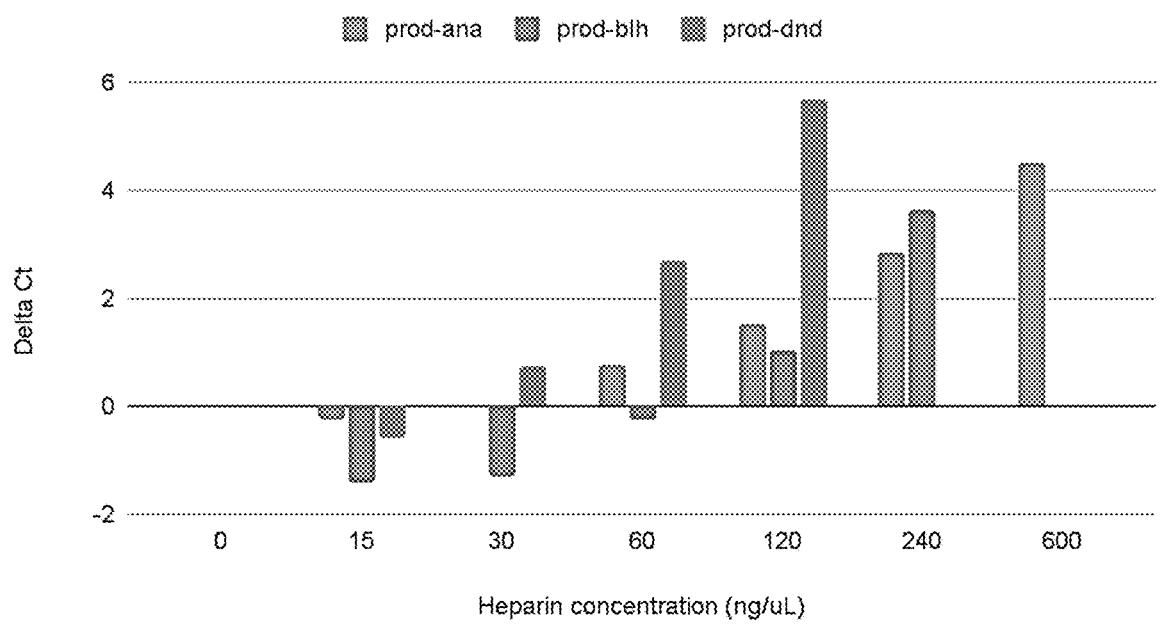
FIG. 4B shows changes in Ct values with increasing heparin concentration for RT enzymes of the disclosure.

FIGS. 4A and 4B show tolerance to inhibition by heparin of embodiments of RT enzymes of the disclosure. FSS was run as described above and in the presence of 0, 15, 30, 60, 120, 240, or 600 ng/uL of heparin. The resulting cDNA values were assessed via Ct values as shown in FIG. 4A.

FIG. 4B shows changes in Ct values with increasing heparin concentration for RT enzymes of the disclosure. Results are summarized below:

1. No inhibition was observed for all RT variants at 15 and 30 ng/uL of heparin.
2. Prod-dnd had the lowest yield (~10 fold or>lower yield) in the presence of>=60 ng/uL and no cDNA was generated at concentrations>120 ng/uL of heparin.
3. Prod-blh had ~4-10 fold lower cDNA yield in the presence of 240 ng/uL compared to prod-ana and no cDNA was generated when 600 ng/uL of heparin was added.
4. Prod-ana had the highest cDNA yield across a broad range of heparin concentrations and cDNA was generated at every heparin concentration tested.

Figure 4C:
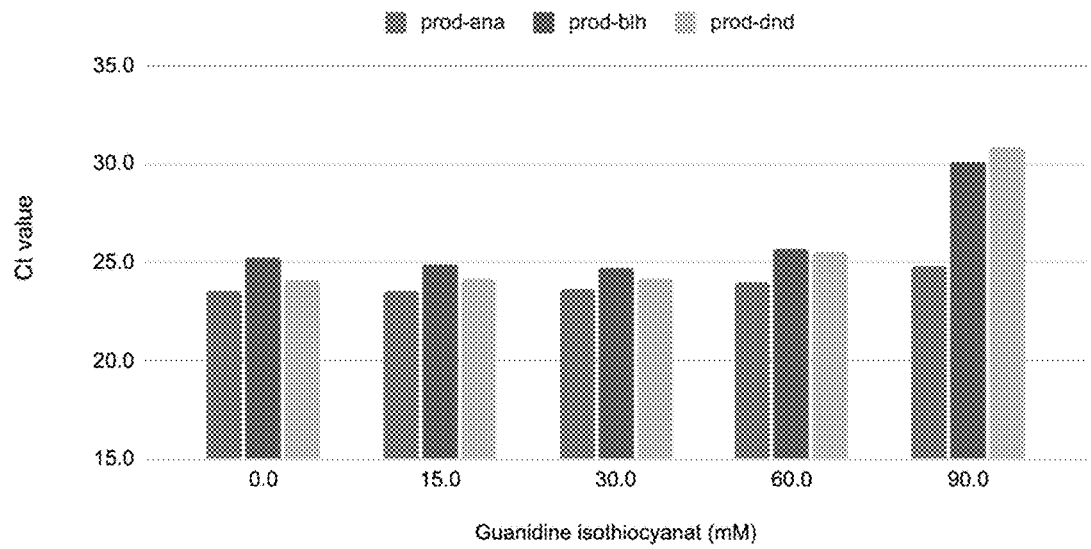
FIG. 4C shows tolerance to inhibition by guanidine isothiocyanate of embodiments of RT enzymes of the disclosure.
Figure 4D:
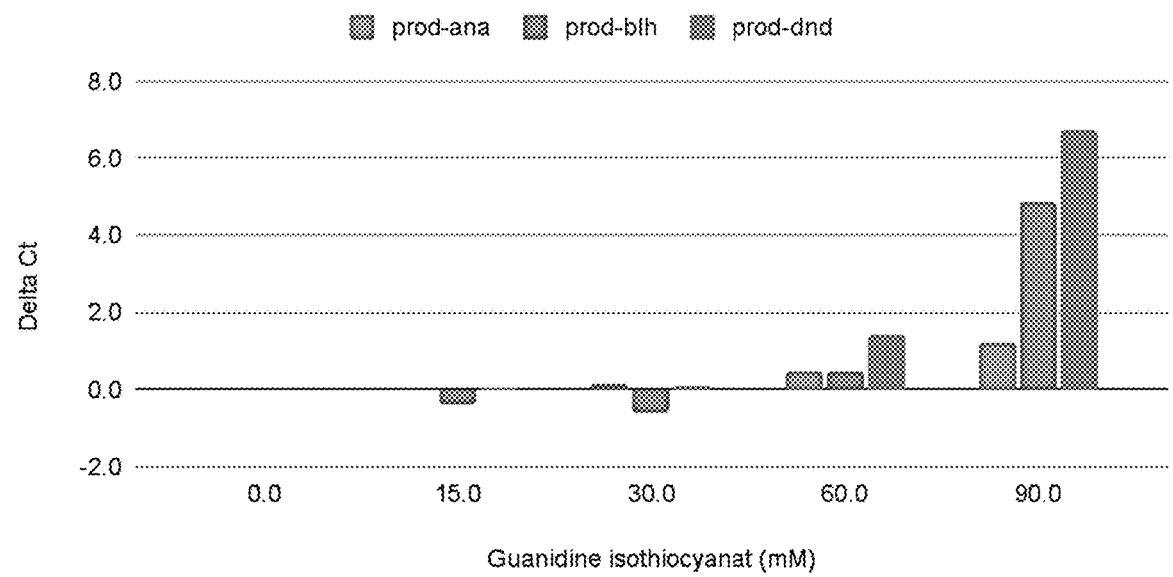
FIG. 4D shows change in Ct values with increasing guanidine isothiocyanate concentration for RT enzymes of the disclosure.

FIGS. 4C and 4D show tolerance to inhibition by guanidine isothiocyanate of embodiments of RT enzymes of the disclosure.

FSS was run as described above in the presence of 0, 15, 30, 60 or 90 mM of guanidine isothiocyanate. The resulting cDNA values were assessed via Ct values as shown in FIG. 4C.

FIG. 4D shows change in Ct values for RT variants of the disclosure with increasing guanidine isothiocyanate concentration. Results are summarized below:
1. No inhibition, or very minimal inhibition, was observed for all RT variants at 30 and 60 mM guanidine isothiocyanate.
2. Prod-dnd showed the greatest inhibition and was inhibited ~4 fold at 60 mM inhibitor and ~100 fold at 90 mM inhibitor.
3. Prod-blh were inhibited by ~4 fold at 60 mM inhibitor and>10 fold at 90 mM inhibitor.
4. Prod-ana had the highest cDNA yield across a broad range of guanidine isothiocyanate concentrations and was inhibited by ~3 fold at 90 mM inhibitor.

Figure 4E:
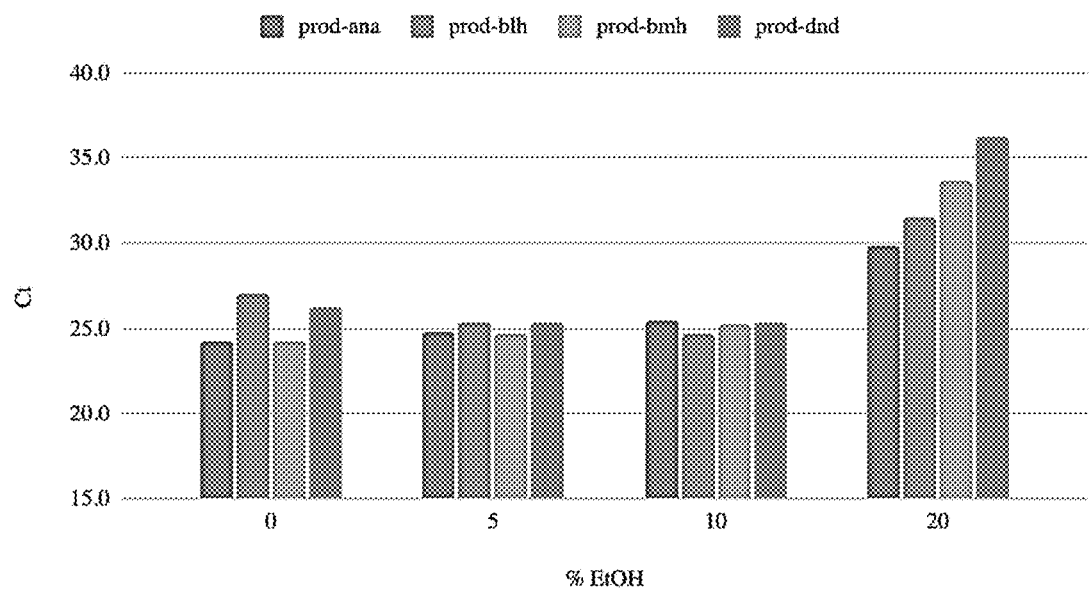
FIG. 4E shows tolerance to inhibition by ethanol of embodiments of RT enzymes of the disclosure.

FIG. 4E shows tolerance to inhibition by ethanol of embodiments of RT enzymes of the disclosure.

FSS was run as described above in the presence of 0, 5, 10 or 20% ethanol. The resulting cDNA values were assessed via Ct values as shown in FIG. 4E.

Figure 4F:
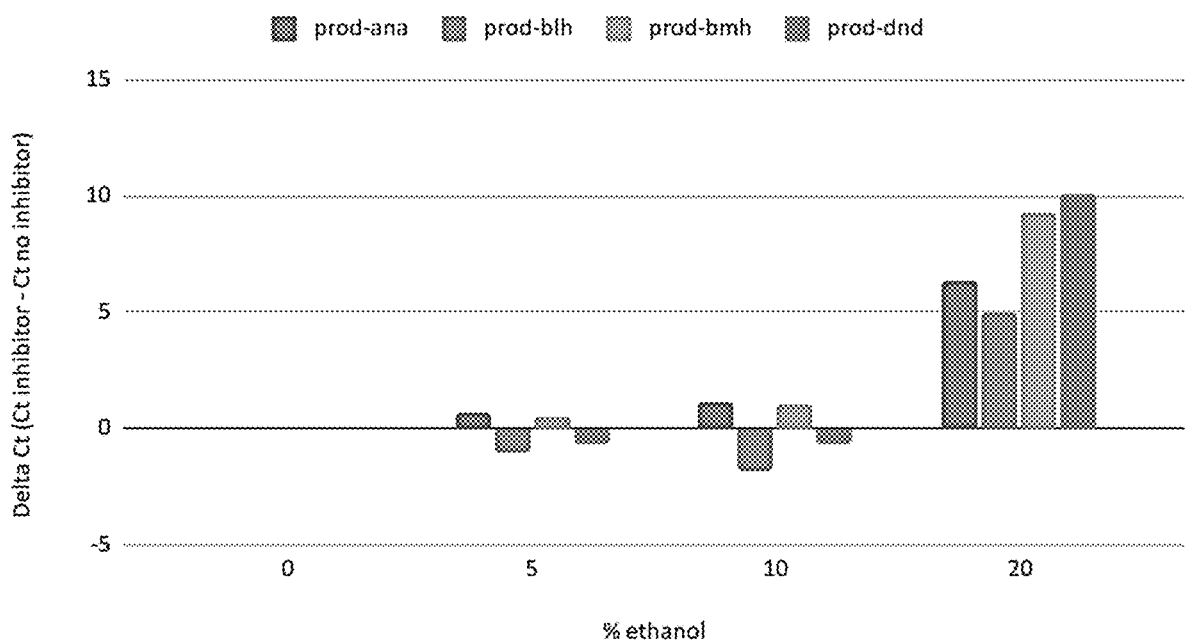
FIG. 4F shows change in Ct values with increasing ethanol concentration for RT enzymes of the disclosure.
Figure 5:
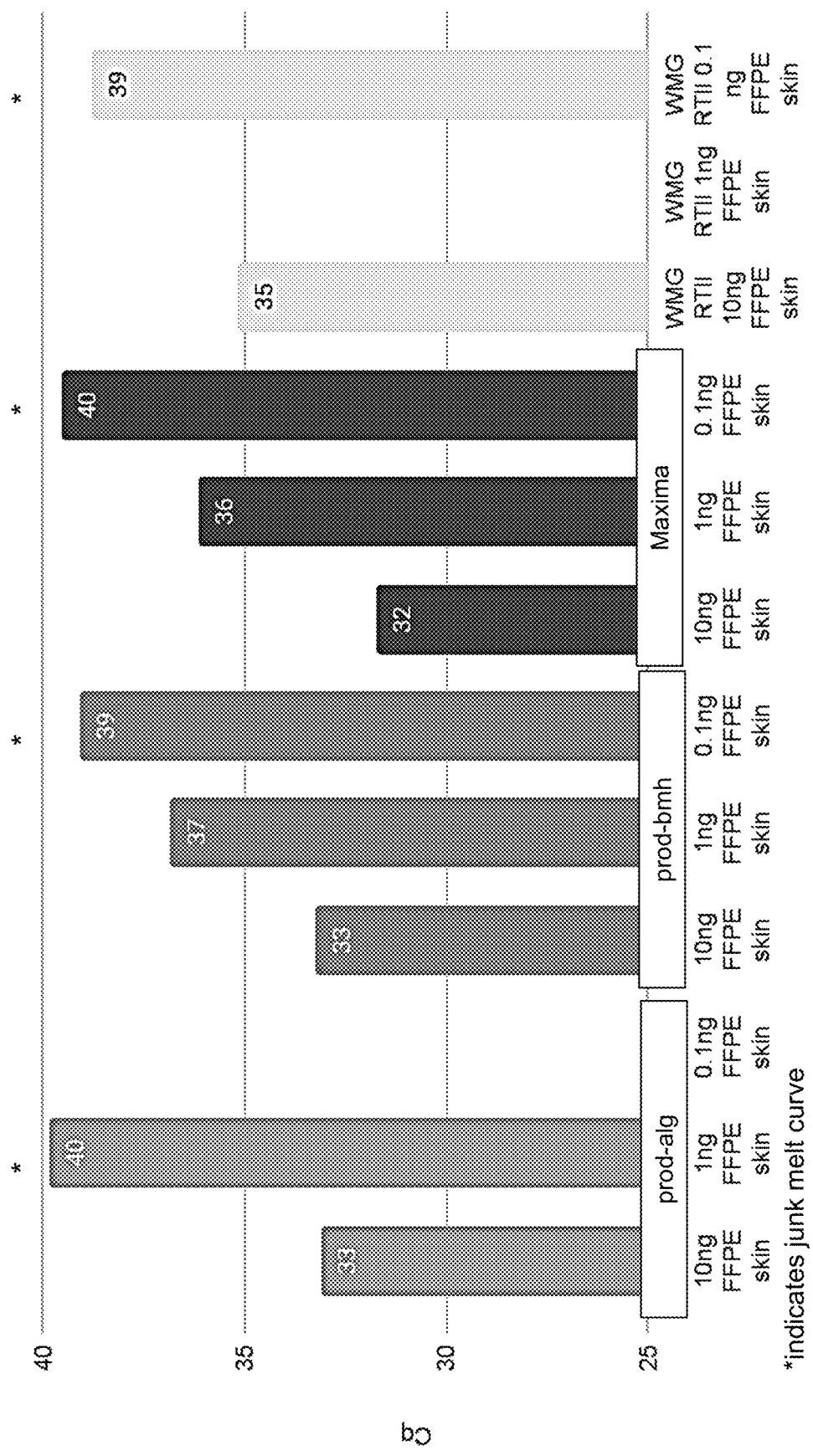
FIG. 5 shows cDNA yields of RT enzymes of the disclosure.

FIG. 4F shows change in Ct values with increasing ethanol concentration for RT enzymes of the disclosure. Results are summarized below:
1. No inhibition, or very minimal inhibition, was observed for all RT variants at 5 and 10% ethanol.
2. Prod-bmh and prod-dnd were inhibited by>~100 fold at 20% ethanol.
3. Prod-ana and Prod-blh were inhibited by<100 fold at 20% ethanol FIG. 5 shows prod-bmh RT has competitive cDNA yields from FFPE samples as Maxima. First strand synthesis (FSS) reactions were generated on ice by mixing 10, 1, or 0.1 ng of FFPE RNA isolated from skin tissue, 1X reaction buffer (50mM Tris-HCl pH 8.3, 75 mM KCl, 3 mM $MgCl_2$), 10U Murine RNase Inhibitor, 5 uM oligo-dT(20), 0.5 mM dNTPs, and 200 U specified reverse transcriptase. FSS was run at 42° C. for 25 minutes followed by qPCR to assess cDNA yield. qPCR reactions were generated by mixing 1X SsoAdvanced Universal SYBR Green Supermix, 10% of the FSS reaction, and 0.6 uM of a primers that anneal to the 5' end of a Beta-actin gene.
Results: The resulting cDNA values were assessed via Ct values and are shown in FIG. 5. Note, asterisk represent a nonspecific melt curve was generated and no specific product was made.
1. Prod-dnd had the lowest yield (~4 fold less than prod-alg and prod-bmh) and only generated specific cDNA product at the 10 ng FFPE RNA input.
2. Prod-alg had equivalent cDNA yields to prod-bmh at 10 ng of FFPE RNA input but was unable to generate specific cDNA product at lower RNA inputs.
3. Prod-bmh generated specific product at 10 ng and 1 ng of FFPE RNA input. cDNA yield was competitive with Maxima RNaseH minus' Reverse Transcriptase.
4. WMG prod-ana has competitive yields and efficiency scores in RT-qPCR as Maxima at 50° C. and 60° C.

Additional further mutations that may optionally be included include one or any combination of S27T, V43K, A46P, L48I, A54P, S56A, S60W, Q68K, L72Q, L72R, E123Q, Y133C, G138S, T163K, M177R, D200H, I212T, I218T, T231E, S232T, L234E, Q237E, A242D, N249E, Q265E, K264Q, K267T, L272I T281S, G290K, N335Q P338E, D339E, Y344F, Q345D E346D, Q349R, Y376F, V413I, T420V, G424D, A442S, V433T, V444I, D518E, G524D, L528F, A554P, Q562E, D583N, K550S, D615E, A619E, F625W/H, R629K, H642D, and K658E.

SEQUENCES

The following sequences may be referred to or used within embodiments of the disclosure. In wtMMLV-RT-aa (SEQ ID NO: 1), position 1 is homologous to position 34 in each of: prod-dnd-aa (SEQ-ID NO 2); prod-ana-aa (SEQ ID NO: 4); prod-amg-aa (SEQ ID NO: 5); prod-asb-aa (SEQ ID NO: 6); prod-bmh-aa (SEQ ID NO: 7); prod-cnc-aa (SEQ ID NO: 8);; prod-cmi-aa (SEQ ID NO: 9); prod-bnb-aa (SEQ ID NO: 10); prod-bsc-aa (SEQ ID NO: 11); prod-csd-aa (SEQ ID NO: 12); and prod-dsf-aa (SEQ ID NO: 13). That is, a position X in SEQ ID NO: 1 is homologous to position X+33 in any of SEQ ID Nos: 2 and 4-14.

```
>wtMMLV-RT-aa
                                        (SEQ ID NO: 1)
TLNIEDEHRL HETSKEPDVS LGSTWLSDFP QAWAETGGMG

LAVRQAPLII PLKATSTPVS IKQYPMSQEA RLGIKPHIQR

LLDQGILVPC QSPWNTPLLP VKKPGTNDYR PVQDLREVNK

RVEDIHPTVP NPYNLLSGLP PSHQWYTVLD LKDAFFCLRL

HPTSQPLFAF EWRDPEMGIS GQLTWTRLPQ GFKNSPTLFD

EALHRDLADF RIQHPDLILL QYVDDLLLAA TSELDCQQGT

RALLQTLGNL GYRASAKKAQ ICQKQVKYLG YLLKEGQRWL

TEARKETVMG QPTPKTPRQL REFLGTAGFC RLWIPGFAEM

AAPLYPLTKT GTLFNWGPDQ QKAYQEIKQA LLTAPALGLP

DLTKPFELFV DEKQGYAKGV LTQKLGPWRR PVAYLSKKLD

PVAAGWPPCL RMVAAIAVLT KDAGKLTMGQ PLVILAPHAV

EALVKQPPDR WLSNARMTHY QALLLDTDRV QFGPVVALNP

ATLLPLPEEG LQHNCLDILA EAHGTRPDLT DQPLPDADHT

WYTDGSSLLQ EGQRKAGAAV TTETEVIWAK ALPAGTSAQR

AELIALTQAL KMAEGKKLNV YTDSRYAFAT AHIHGEIYRR

RGLLTSEGKE IKNKDEILAL LKALFLPKRL SIIHCPGHQK

GHSAEARGNR MADQAARKAA ITETPDTSTL L
```

>prod-dnd-aa (SEQ-ID NO 2)

MGGSHHHHHH GMASMTGGQQ MGRDLYDDDD KHMTLNIEDE
HRLHETSKEP DVSLGSTWLS DFPQAWAETG GMGLAVRQAP
LIIPLKATST PVSIKQYPMS QEARLGIKPH IQRLLDQGIL
VPCQSPWNTP LLPVKKPGTN DYRPVQDLRE VNKRVEDIHP
TVPNPYNLLS GLPPSHQWYT VLDLKDAFFC LRLHPTSQPL
FAFEWRDPEM GISGQLTWTR LPQGFKNSPT LFDEALHRDL
ADFRIQHPDL ILLQYVDDLL LAATSELDCQ QGTRALLQTL
GNLGYRASAK KAQICQKQVK YLGYLLKEGQ RWLTEARKET
VMGQPTPKTP RQLREFLGTA GFCRLWIPGF AEMAAPLYPL
TKTGTLFNWG PDQQKAYQEI KQALLTAPAL GLPDLTKPFE
LFVDEKQGYA KGVLTQKLGP WRRPVAYLSK KLDPVAAGWP
PCLRMVAAIA VLTKDAGKLT MGQPLVILAP HAVEALVKQP
PDRWLSNARM THYQALLLDT DRVQFGPVVA LNPATLLPLP
EEGLQHNCLD ILAEAHGTRP DLTDQPLPDA DHTWYTGGSS
LLQEGQRKAG AAVTTETEVI WAKALPAGTS AQRAQLIALT
QALKMAEGKK LNVYTNSRYA FATAHIHGEI YRRRGLLTSE
GKEIKNKDEI LALLKALFLP KRLSIIHCPG HQKGHSAEAR
GNRMADQAAR KAAITETPDT STLL

>prod-dnd-nt (SEQ-ID NO 3)

ATGGGGGGTT CTCATCATCA TCATCATCAT GGTATGGCTA
GCATGACTGG TGGACAGCAA ATGGGTCGGG ATCTGTACGA
CGATGACGAT AAGCATATGA CCCTAAATAT AGAAGATGAG
CACCGGCTAC ATGAGACCTC AAAAGAGCCA GATGTTTCTC
TAGGGTCCAC ATGGTTATCG GATTTCCCGC AAGCTTGGGC
TGAAACGGGG GGTATGGGGC TTGCTGTACG CCAGGCGCCC
CTTATTATTC CTCTTAAGGC AACAAGCACC CCCGTCAGCA
TCAAACAATA CCCCATGTCA CAAGAAGCGC GTTTGGGTAT
TAAACCGCAC ATTCAACGCT TGCTGGACCA AGGGATCCTT
GTCCCCTGTC AGTCTCCATG GAACACGCCG CTGTTACCGG
TCAAGAAGCC TGGTACAAAC GACTACCGTC CTGTACAGGA
TTTGCGCGAG GTAAATAAGC GTGTAGAGGA TATCCACCCC
ACCGTGCCCA ACCCATACAA CTTGTTGTCT GGTTTACCGC
CTTCACATCA GTGGTATACG GTCCTTGATT TGAAAGATGC
ATTTTTCTGC CTGCGCTTGC ACCCTACGTC TCAGCCACTG
TTCGCATTCG AGTGGCGCGA CCCTGAAATG GGTATCAGTG
GTCAGTTAAC CTGGACACGC TTACCGCAAG GTTTCAAGAA
TAGCCCGACC TTATTCGATG AAGCACTTCA CCGCGATCTT
GCCGATTTCC GCATCCAGCA CCCGGATCTT ATTTTGTTGC
AGTACGTAGA CGACCTGTTG TTGGCAGCCA CGTCGGAATT
GGATTGTCAG CAAGGAACAC GCGCGTTACT GCAAACTCTG
GGTAATTTGG GCTACCGTGC CTCCGCAAAG AAAGCGCAGA
TCTGCCAAAA GCAAGTAAAA TACTTAGGAT ATTTATTGAA
GGAGGGCCAG CGTTGGCTTA CAGAAGCTCG CAAAGAAACT
GTGATGGGAC AACCTACGCC TAAAACTCCT CGTCAGCTTC
GCGAATTCCT GGGAACAGCG GGGTTCTGTC GCCTGTGGAT
TCCTGGTTTT GCAGAGATGG CGGCGCCCCT TTACCCACTG
ACCAAAACAG GGACATTATT AACTGGGGT CCCGATCAGC
AGAAGGCCTA TCAGGAGATC AAGCAGGCTT TACTTACAGC
GCCAGCCTTA GGGTTACCGG ACCTTACGAA GCCCTTTGAG
TTATTCGTCG ACGAGAAACA GGGCTATGCA AAGGGTGTAC
TGACCCAGAA GTTGGGGCCG TGGCGTCGCC CGGTCGCCTA
TTTGTCGAAA AAACTGGATC CCGTGGCGGC CGGGTGGCCA
CCTTGCCTGC GTATGGTTGC AGCTATTGCT GTATTAACAA
AAGACGCAGG AAAATTAACG ATGGGACAAC CGTTAGTCAT
TCTTGCGCCG CACGCAGTAG AAGCACTGGT AAAGCAACCG
CCCGATCGCT GGTTATCGAA CGCGCGCATG ACGCACTATC
AGGCGTTGTT ACTTGATACA GATCGTGTAC AGTTTGGCCC
TGTCGTTGCA TTGAACCCAG CCACGCTGTT ACCTCTTCCG
GAAGAAGGAT TACAACACAA CTGTCTGGAC ATCCTGGCGG
AAGCTCATGG AACCCGCCCT GACTTGACAG ACCAACCGTT
ACCCGACGCT GATCATACCT GGTATACCGG GGGTTCGTCG
CTTTTGCAGG AAGGGCAACG TAAGGCAGGT GCAGCCGTAA
CGACCGAGAC CGAAGTCATC TGGGCCAAGG CCTTGCCAGC
GGGGACTAGT GCCCAGCGTG CCCAATTAAT TGCCCTTACG
CAGGCATTAA AGATGGCTGA AGGAAAAAAG CTGAATGTAT
ACACTAACAG CCGCTACGCG TTCGCGACAG CGCATATTCA
TGGAGAGATC TACCGTCGCC GCGGACTTCT TACCTCCGAG
GGTAAGGAGA TTAAGAACAA AGATGAGATT CTGGCTTTGT
TGAAGGCGTT GTTTTTGCCC AAACGTTTGT CAATCATTCA
CTGTCCCGGG CATCAAAAAG GCACAGCGC GAGGCCCGT
GGTAACCGTA TGGCAGACCA GGCCGCACGT AAAGCAGCCA
TTACGGAGAC ACCTGATACG AGTACGTTAC TTTAA

>prod-ana-aa (SEQ ID NO: 4)

MGGSHHHHHHGMASMTGGQQMGRDLYDDDDKHMTLNIEDEHRLHETSKEP
DVSLGSTWLSDFPQAWAETGGMGLAVRQAPLIIPLKATATPVSIKQYPMS
QEARQGIKPHIQRLLDQGILVPCQSPWNTPLLPVKKPGTNDYRPVQDLRE
VNKRVEDIHPTVPNPYNLLSSLPPSHQWYTVLDLKDAFFCLRLHPKSQPL

```
FAFEWRDPEMGISGQLTWTRLPQGFKNSPTLFDEALRRDLADFRIQHPDL
ILLQYVDDLLLAATTEEDCQQGTRALLQTLGELGYRASAKKAQICQKQVK
YLGYLLKEGQRWLTEARKETVMKQPTPKTPRQLREFLGKAGFCRLWIPGF
AEMAAPLYPLTKTGTLFNWGPDQQKAFQEIKQALLTAPALGLPDLTKPFE
LFVDEKQGYAKGVLTQKLGPWRRPVAYLSKKLDPVAAGWPPCLRMVAAIA
VLVKDADKLTMGQPLVILAPHAVEALIKQPPDRWLSNARMTHYQALLLDT
DRVQFGPVVALNPATLLPLPEEGLQHNCLDILAEAHGTRPDLTDQPLPDA
DHTWYTGGSSLLQEGQRKAGAAVTTETEVIWAKALPAGTSAQRAQLIALT
QALKMAEGKKLNVYTNSRYAFATAHIHGEIYRRRGLLTSEGKEIKNKEEI
LALLKALFLPKRLSIIHCPGHQKGDSAEARGNRMADQAARKAAITETPDT
STLLIENSSPNSRLIN
```

>prod-amg-aa
(SEQ ID NO: 5)
```
MGGSHHHHHH GMASMTGGQQ MGRDLYDDDD KHMTLNIEDE
HRLHETSKEP DVSLGSMTWL SDFPQAWAET GGMGLAVRQA
PLIIPLKATA TPVSIKQYPM SQEARLGIKP HIQRLLDQGI
LVPCQSPWNT PLLPVKKPGT NDYRPVQDLR EVNKRVEDIH
PTVPNPYNLL SSLPPSHQWY TVLDLKDAFF CLRLHPTSQP
LFAFEWRDPE MGISGQLTWT RLPQGFKNSP TLFDEALHRD
LADFRIQHPD LILLQYVDDL LLAATTEEDC QQGTRALLQT
LGNLGYRASA KKAQICQKQV KYLGYLLKEG QRWLTEARKE
TVMKQPTPKT PRQLREFLGT AGFCRLWIPG FAEMAAPLYP
LTKTGTLFNW GPDQQKAFQE IKQALLTAPA LGLPDLTKPF
ELFVDEKQGY AKGVLTQKLG PWRRPVAYLS KKLDPVAAGW
PPCLRMVAAI AVLVKDADKL TMGQPLVILA PHAVEALIKQ
PPDRWLSNAR MTHYQALLLD TDRVQFGPVV ALNPATLLPL
PEEGLQHNCL DILAEAHGTR PDLTDQPLPD ADHTWYTGGS
SLLQEGQRKA GAAVTTETEV IWAKALPAGT SAQRAQLIAL
TQALKMAEGK KLNVYTNSRY AFATAHIHGE IYRRRGLLTS
EGKEIKNKEE ILALLKALFL PKRLSIIHCP GHQKGHSAEA
RGNRMADQAA RKAAITETPD TSTLLIENSS PNSRLIN
```

>prod-asb-aa
(SEQ ID NO: 6)
```
MGGSHHHHHH GMASMTGGQQ MGRDLYDDDD KHMTLNIEDE
HRLHETSKEP DVSLGSTWLT DFPQAWAETG GMGLAKRQPP
IIIPLKPTAT PVWIKQYPMS KEARQGIKPH IQRLLDQGIL
VPCQSPWNTP LLPVKKPGTN DYRPVQDLRE VNKRVQDIHP
TVPNPCNLLS SLPPSHQWYT VLDLKDAFFC LRLHPKSQPL
FAFEWRDPER GISGQLTWTR LPQGFKNSPT LFHEALHRDL
ADFRTQHPDL TLLQYVDDLL LAAETEEDCE QGTRDLLQTL
```

>prod-bmh-aa
(SEQ ID NO: 7)
```
GELGYRASAK KAQICQQEVT YLGYILKEGQ RWLSEARKET
VMKQPTPKTP RQLREFLGTA GFCRLWIPGF AEMAAPLYPL
TKTGTLFQWG EEQQKAFDDI KRALLTAPAL GLPDLTKPFE
LFVDEKQGFA KGVLTQKLGP WRRPVAYLSK KLDPVAAGWP
PCLRMIAAIA VLVKDADKLT MGQPLTILAP HAVESLIKQP
PDRWLSNARM THYQALLLDT DRVQFGPVVA LNPATLLPLP
EEGLQHNCLD ILAEAHGTRP DLTDQPLPDA EHTWYTGGSS
FLQEGQRKAG AAVTTETEVI WASALPPGTS AQRAQLIALT
QALKMAEGKK LNVYTNSRYA FATAHIHGEI YRRRGLLTSE
GKEIKNKEEI LELLKALWLP KKLAIIHCPG HQKGDSAEAR
GNRMADQAAR EAAITETPDT STLLIENSSP NSRLIN
```

>prod-cnc-aa
(SEQ ID NO: 8)
```
MGGSHHHHHH GMASMTGGQQ MGRDLYDDDD KHMTLNIEDE
HRLHETSKEP DVSLGSTWLS DFPQAWAETG GMGLAKRQAP
LIIPLKATAT PVSIKQYPMS QEARQGIKPH IQRLLDQGIL
VPCQSPWNTP LLPVKKPGTN DYRPVQDLRE VNKRVEDIHP
TVPNPYNLLS SLPPSHQWYT VLDLKDAFFC LRLHPKSQPL
FAFEWRDPEM GISGQLTWTR LPQGFKNSPT LFDEALRRDL
ADFRIQHPDL ILLQYVDDLL LAATTEEDCE QGTRALLQTL
```

-continued
```
GELGYRASAK KAQICQKEVK YLGYLLKEGQ RWLTEARKET
VMKQPTPKTP RQLREFLGKA GFCRLWIPGF AEMAAPLYPL
TKTGTLFNWG PDQQKAFQEI KQALLTAPAL GLPDLTKPFE
LFVDEKQGVA KGVLTQKLGP WRRPVAYLSK KLDPVAAGWP
PCLRMVAAIA VLVKDADKLT MGQPLVILAP HAVEALIKQP
PDRWLSNARM THYQALLLDT DRVQFGPVVA LNPATLLPLP
EEGLQHNCLD ILAEAHGTRP DLTDQPLPDA DHTWYTGGSS
FLQEGQRKAG AAVTTETEVI WAKALPAGTS AQRAQLIALT
QALKMAEGKK LNVYTNSRYA FATAHIHGEI YRRRGLLTSE
GKEIKNKEEI LALLKALFLP KRLSIIHCPG HQKGDSAEAR
GNRMADQAAR KAAITETPDT STLLIENSSP NSRLIN
```

>prod-cmi-aa
(SEQ ID NO: 9)
```
MGGSHHHHHH GMASMTGGQQ MGRDLYDDDD KHMTLNIEDE
HRLHETSKEP DVSLGSMTWL SDFPQAWAET GGMGLAVRQA
PLIIPLKATA TPVSIKQYPM SQEARLGIKP HIQRLLDQGI
LVPCQSPWNT PLLPVKKPGT NDYRPVQDLR EVNKRVEDIH
PTVPNPYNLL SSLPPSHQWY TVLDLKDAFF CLRLHPTSQP
LFAFEWRDPE MGISGQLTWT RLPQGFKNSP TLFDEALRRD
LADFRIQHPD LILLQYVDDL LLAATTEEDC QQGTRALLQT
LGNLGYRASA KKAQICQKQV KYLGYLLKEG QRWLTEARKE
TVMKQPTPKT PRQLREFLGK AGNCRLWIPG FAEMAAPLYP
LTKTGTLFNW GPDQQKAFQE IKQALLTAPA LGLPDLTKPF
ELFVDEKQGY AKGVLTQKLG PWRRPVAYLS KKLDPVAAGW
PPCLRMVAAI AVLVKDADKL TMGQPLVILA PHAVEALIKQ
PPDRWLSNAR MTHYQALLLD TDRVQFGPVV ALNPATLLPL
PEEGLQHNCL DILAEAHGTR PDLTDQPLPD ADHTWYTGGS
SLLQEGQRKA GAAVTTETEV IWAKALPAGT SAQRAQLIAL
TQALKMAEGK KLNVYTNSRY AFATAHIHGE IYRRRGLLTS
EGKEIKNKEE ILALLKALFL PKRLSIIHCP GHQKGHSAEA
RGNRMADQAA RKAAITETPD TSTLLIENSS PNSRLIN
```

>prod-bnb-aa
(SEQ ID NO: 10)
```
MGGSHHHHHH GMASMTGGQQ MGRDLYDDDD KHMTLNIEDE
HRLHETSKEP DVSLGSTWLS DFPQAWAETG GMGLAVRQAP
LIIPLKATAT PVSIKQYPMS QEARQGIKPH IQRLLDQGIL
VPCQSPWNTP LLPVKKPGTN DYRPVQDLRE VNKRVEDIHP
TVPNPYNLLS SLPPSHQWYT VLDLKDAFFC LRLHPKSQPL
FAFEWRDPEM GISGQLTWTR LPQGFKNSPT LFDEALRRDL
ADFRIQHPDL ILLQYVDDLL LAATTEEDCQ QGTRALLQTL
```

-continued
```
GELGYRASAK KAQICQKQVK YLGYLLKEGQ RWLTEARKET
VMKQPTPKTP RQLREFLGKA GNCRLWIPGF AEMAAPLYPL
TKTGTLFNWG PDQQKAFQEI KQALLTAPAL GLPDLTKPFE
LFVDEKQGYA KGVLTQKLGP WRRPVAYLSK KLDPVAAGWP
PCLRMVAAIA VLVKDADKLT MGQPLVILAP HAVEALIKQP
PDRWLSNARM THYQALLLDT DRVQFGPVVA LNPATLLPLP
EEGLQHNCLD ILAEAHGTRP DLTDQPLPDA DHTWYTGGSS
LLQEGQRKAG AAVTTETEVI WAKALPAGTS AQRAQLIALT
QALKMAEGKK LNVYTNSRYA FATAHIHGEI YRRRGLLTSE
GKEIKNKEEI LALLKALFLP KRLSIIHCPG HQKGDSAEAR
GNRMADQAAR KAAITETPDT STLLIENSSP NSRLIN
```

>prod-bsc-aa
(SEQ ID NO: 11)
```
MGGSHHHHHH GMASMTGGQQ MGRDLYDDDD KHMTLNIEDE
HRLHETSKEP DVSLGSTWLT DFPQAWAETG GMGLAKRQPP
IIIPLKPTAT PVWIKQYPMS KEARQGIKPH IQRLLDQGIL
VPCQSPWNTP LLPVKKPGTN DYRPVQDLRE VNKRVQDIHP
TVPNPCNLLS SLPPSHQWYT VLDLKDAFFC LRLHPKSQPL
FAFEWRDPER GISGQLTWTR LPQGFKNSPT LFHEALRRDL
ADFRTQHPDL TLLQYVDDLL LAAETEEDCE QGTRDLLQTL
GELGYRASAK KAQICQQEVT YLGYILKEGQ RWLSEARKET
VMKQPTPKTP RQLREFLGKA GFCRLWIPGF AEMAAPLYPL
TKTGTLFQWG EEQQKAFDDI KRALLTAPAL GLPDLTKPFE
LFVDEKQGFA KGVLTQKLGP WRRPVAYLSK KLDPVAAGWP
PCLRMIAAIA VLVKDADKLT MGQPLTILAP HAVESLIKQP
PDRWLSNARM THYQALLLDT DRVQFGPVVA LNPATLLPLP
EEGLQHNCLD ILAEAHGTRP DLTDQPLPDA EHTWYTGGSS
FLQEGQRKAG AAVTTETEVI WASALPPGTS AQRAQLIALT
QALKMAEGKK LNVYTNSRYA FATAHIHGEI YRRRGLLTSE
GKEIKNKEEI LELLKALWLP KKLAIIHCPG HQKGDSAEAR
GNRMADQAAR EAAITETPDT STLLIENSSP NSRLIN
```

>prod-csd-aa
(SEQ ID NO: 12)
```
MGGSHHHHHH GMASMTGGQQ MGRDLYDDDD KHMTLNIEDE
HRLHETSKEP DVSLGSTWLT DFPQAWAETG GMGLAKRQPP
IIIPLKPTAT PVWIKQYPMS KEARQGIKPH IQRLLDQGIL
VPCQSPWNTP LLPVKKPGTN DYRPVQDLRE VNKRVQDIHP
TVPNPCNLLS SLPPSHQWYT VLDLKDAFFC LRLHPKSQPL
FAFEWRDPER GISGQLTWTR LPQGFKNSPT LFHEALRRDL
ADFRTQHPDL TLLQYVDDLL LAAETEEDCE QGTRDLLQTL
```

-continued
```
GELGYRASAK KAQICQQEVT YLGYILKEGQ RWLSEARKET
VLKQPTPKTP RQLREFLGKA GNCRLWIPGF AEMAAPLYPL
TKTGTLFQWG EEQQKAFDDI KRALLTAPAL GLPDLTKPFE
LFVDEKQGFA KGVLTQKLGP WRRPVAYLSK KLDPVAAGWP
PCLRMIAAIA VLVKDADKLT MGQPLTILAP HAVESLIKQP
PDRWLSNARM THYQALLLDT DRVQFGPVVA LNPATLLPLP
EEGLQHNCLD ILAEAHGTRP DLTDQPLPDA EHTWYTGGSS
FLQEGQRKAG AAVTTETEVI WASALPPGTS AQRAQLIALT
QALKMAEGKK LNVYTNSRYA FATAHIHGEI YRRRGLLTSE
GKEIKNKEEI LELLKALWLP KKLAIIHCPG HQKGDSAEAR
GNRMADQAAR EAAITETPDT STLLIENSSP NSRLIN
```

>prod-dsf-aa
(SEQ ID NO: 13)
```
MGGSHHHHHH GMASMTGGQQ MGRDLYDDDD KHMTLNIEDE
HRLHETSKEP DVSLGSTWLS DFPQAWAETG GMGLAKRQAP
LIIPLKPTAT PVWIKQYPMS QEARQGIKPH IQRLLDQGIL
VPCQSPWNTP LLPVKKPGTN DYRPVQDLRE VNKRVEDIHP
TVPNPYNLLS SLPPSHQWYT VLDLKDAFFC LRLHPKSQPL
FAFEWRDPEM GISGQLTWTR LPQGFKNSPT LFHEALHRDL
ADFRIQHPDL ILLQYVDDLL LAATTEEDCE QGTRALLQTL
GELGYRASAK KAQICQKEVT YLGYLLKEGQ RWLTEARKET
VMKQPTPKTP RQLREFLGTA GFCRLWIPGF AEMAAPLYPL
TKTGTLFNWG PEQQKAFQEI KQALLTAPAL GLPDLTKPFE
LFVDEKQGFA KGVLTQKLGP WRRPVAYLSK KLDPVAAGWP
PCLRMVAAIA VLVKDADKLT MGQPLTILAP HAVEALIKQP
PDRWLSNARM THYQALLLDT DRVQFGPVVA LNPATLLPLP
EEGLQHNCLD ILAEAHGTRP DLTDQPLPDA DHTWYTGGSS
FLQEGQRKAG AAVTTETEVI WAKALPPGTS AQRAQLIALT
QALKMAEGKK LNVYTNSRYA FATAHIHGEI YRRRGLLTSE
GKEIKNKEEI LALLKALWLP KRLSIIHCPG HQKGDSAEAR
GNRMADQAAR EAAITETPDT STLLIENSSP NSRLIN
```

>prod-blh
(SEQ ID NO: 14)
```
MGGSHHHHHHGMASMTGGQQMGRDLYDDDDKHMTLNIEDEHRLHE
TSKEPDVSLGSTWLSDFPQAWAETGGMGLAVRQAPLIIPLKATSTPVSIK
QYPMSQEARLGIKPHIQRLLDQGILVPCQSPWNTPLLPVKKPGTNDYRPV
QDLREVNKRVEDIHPTVPNPYNLLSGLPPSHQWYTVLDLKDAFFCLRLHP
TSQPLFAFEWRDPEMGISGQLTWTRLPQGFKNSPTLFDEALRRDLADFRI
QHPDLILLQYVDDLLLAATSELDCQQGTRALLQTLGNLGYRASAKKAQIC
QKQVKYLGYLLKEGQRWLTEARKETVMGQPTPKTPRQLREFLGKAGNCRL
WIPGFAEMAAPLYPLTKTGTLFNWGPDQQKAYQEIKQALLTAPALGLPDL
TKPFELFVDEKQGYAKGVLTQKLGPWRRPVAYLSKKLDPVAAGWPPCLRM
VAAIAVLTKDAGKLTMGQPLVILAPHAVEALVKQPPDRWLSNARMTHYQA
LLLDTDRVQFGPVVALNPATLLPLPEEGLQHNCLDILAEAHGTRPDLTDQ
PLPDADHTWYTGGSSLLQEGQRKAGAAVTTETEVIWAKALPAGTSAQRAQ
LIALTQALKMAEGKKLNVYTNSRYAFATAHIHGEIYRRRGLLTSEGKEIK
NKDEILALLKALFLPKRLSIIHCPGHQKGHSAEARGNRMADQAARKAAIT
ETPDTSTLL
```

>prod-ajw
(SEQ ID NO: 15)
```
MGGSHHHHHHGMASMTGGQQMGRDLYDDDDKHMTLNIEDEHRLHE
TSKEPDVSLGSTWLSDFPQAWAETGGMGLAVRQAPLIIPLKATSTPVSIK
QYPMSQEARQGIKPHIQRLLDQGILVPCQSPWNTPLLPVKKPGTNDYRPV
QDLREVNKRVEDIHPTVPNPYNLLSSLPPSHQWYTVLDLKDAFFCLRLHP
KSQPLFAFEWRDPEMGISGQLTWTRLPQGFKNSPTLFDEALHRDLADFRI
QHPDLILLQYVDDLLLAATTEEDCQQGTRALLQTLGELGYRASAKKAQIC
QKQVKYLGYLLKEGQRWLTEARKETVMKQPTPKTPRQLREFLGTAGFCRL
WIPGFAEMAAPLYPLTKTGTLFNWGPDQQKAFQEIKQALLTAPALGLPDL
TKPFELFVDEKQGYAKGVLTQKLGPWRRPVAYLSKKLDPVAAGWPPCLRM
VAAIAVLVKDADKLTMGQPLVILAPHAVEALIKQPPDRWLSNARMTHYQA
LLLDTDRVQFGPVVALNPATLLPLPEEGLQHNCLDILAEAHGTRPDLTDQ
PLPDADHTWYTGGSSLLQEGQRKAGAAVTTETEVIWAKALPAGTSAQRAQ
LIALTQALKMAEGKKLNVYTNSRYAFATAHIHGEIYRRRGLLTSEGKEIK
NKEEILALLKALFLPKRLSIIHCPGHQKGDSAEARGNRMADQAARKAAIT
ETPDTSTLLIENSSPNSRLIN
```

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A modified reverse transcriptase comprising at least one modification in a reverse transcriptase sequence as set forth in SEQ ID NO: 2, wherein the modified reverse transcriptase exhibits an increased thermal stability relative to the reverse transcriptase as set forth in SEQ ID NO: 2 such that an activity of the reverse transcriptase at temperatures of about 50° C. or greater is at least 90% of the reverse transcription activity of the reverse transcriptase shown in SEQ ID NO: 2 at 42° C., wherein the modification comprises an amino acid substitution selected from the group consisting of:

S at position 56 substituted with G, A, V, L, or I;
L at position 72 substituted with Q;
G at position 138 substituted with S, C, T, or M;
H at position 204 substituted with K or R;
S at position 232 substituted with C, T, or M;
L at position 234 substituted with N, or Q;
G at position 290 substituted with H, or R;
T at position 306 substituted with H, or R;
Y at position 344 substituted with F or M;
T at position 420 substituted with G, A, V, L, or I;
G at position 424 substituted with D, E, N, or Q;
V at position 444 substituted with G, A, L, or I;
D at position 524 substituted with G, V, or I;
E at position 562 substituted with D, N, or Q;
D at position 583 substituted with E, or Q;
D at position 615 substituted with E, N, or Q; and
H at position 642 substituted with D, E, N, or Q.

2. The modified reverse transcriptase of claim 1, wherein, the modification further comprises an amino acid substitution at an amino acid position selected from positions 27, 200, 212, 218, 231, 237, 242, 249, 264, 265, 267, 272, 43, 46, 48, 54, 163, 177, 280, 281, 335, 338, 339, 345, 346, 349, 376, 413, 443, 518, 528, 550, 554, 619, 625, 629, and 658 of SEQ ID NO: 2.

3. The modified reverse transcriptase of claim 1, wherein the number of substitutions range from at least 3 amino acid positions to at least 14 amino acid positions.

4. The modified reverse transcriptase of claim 1, wherein the amino acid substitution is selected from S56A, G138S, S232T, L234E, G290K, Y344F, T420V, G424D, V444I, and D615E.

5. The modified reverse transcriptase of claim 2, wherein at least one amino acid substitution is selected from G524D, N583D, and Q562E.

6. The modified reverse transcriptase of claim 2, wherein the amino acid substitution is selected from L72Q, T163K, N249E, and H642D.

7. The modified reverse transcriptase of claim 2, wherein the amino acid substitution is selected from S56A, G138S, S232T, L234E, G290K, Y344F, T420V, G424D, V444I, D615E, and H642D.

8. The modified reverse transcriptase of claim 7, further comprising at least one additional amino acid substitution selected from G524D, N583D, Q562E, R204H, and K306T.

9. The modified reverse transcriptase of claim 2, wherein the amino acid substitution is selected from S27T, V43K, A46P, L48I, A54S, S56A, L72Q, G138S, T163K, M177R, D200H, I212T, I218T, T231E, S232T, L234E, Q237E, A242D, N249E, Q265E, K264Q, K267T, L272I T281S, G290K, N335Q, P338E, D339E, Y344F, Q345D E346D, Q349R, Y376F, V413I, T420V, G424D, A442S, V433T, V444I, D518E, G524D, L528F, A554P, E562Q, D583N, K550S, D615E, A619E, F625W/H, R629K, H642D, and K658E.

10. The modified reverse transcriptase of claim 1, wherein the activity of the reverse transcriptase at temperatures of 65° C. or greater is at least 50% of the reverse transcription activity of the reverse transcriptase as set forth shown in SEQ ID NO: 2 at 42° C.

11. The modified reverse transcriptase of claim 1, wherein the activity of the reverse transcriptase is improved compared to the reverse transcriptase shown in SEQ ID NO: 2 in the presence of inhibitors of reverse transcription.

12. The modified reverse transcriptase of claim 1, wherein the reverse transcriptase exhibits increased thermal stability relative to the reverse transcriptase of SEQ ID NO: 2, further comprising at least one amino acid substitution selected from the group consisting of E5K; M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

13. The modified reverse transcriptase of claim 1, wherein the reverse transcription activity of the reverse transcriptase is improved in the presence of inhibitors of reverse transcription relative to the reverse transcriptase of SEQ ID NO:

2, further comprising at least one amino acid substitution selected from the group consisting of M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; L528I; H594R, H594K or H594Q; L603W or L603M; E607K, E607G or E607A; H634Y; A644V or A644T; N649S; D653G, D653A, D653H or D653V; K658R or K658Q; and L671P.

14. The modified reverse transcriptase of claim 1, wherein the reverse transcription activity of the reverse transcriptase is improved in formalin-fixed samples relative to the reverse transcriptase of SEQ ID NO: 2, further comprising at least one amino acid substitution selected from the group consisting of M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; L528I; H594R, H594K or H594Q; L603W or L603M; E607K, E607G or E607A; H634Y; A644V or A644T; N649S; D653G, D653A, D653H or D653V; K658R or K658Q; and L671P.

15. The modified reverse transcriptase of claim 1, wherein the reverse transcriptase exhibits increased thermal stability relative to the reverse transcriptase of SEQ ID NO: 2, further comprising at least one amino acid substitution selected from the group consisting of A32V, E286R, E302K, W388R, and L435R.

16. The modified reverse transcriptase of claim 1, wherein the activity of the reverse transcriptase is improved compared in the presence of inhibitors of reverse transcription relative to the reverse transcriptase of SEQ ID NO: 2, further comprising at least one amino acid substitution selected from the group consisting of A32V, E286R, E302K, W388R, and L435R.

17. The modified reverse transcriptase of claim 1, wherein the reverse transcription activity of the reverse transcriptase is improved for formalin-fixed samples relative to the reverse transcriptase of SEQ ID NO: 2, further comprising at least one amino acid substitution selected from the group consisting of A32V, E286R, E302K, W388R, and L435R.

18. The modified reverse transcriptase of claim 1, wherein the modified reverse transcriptase comprises a sequence of amino acids having at least 95% sequence identity with the wild type Moloney Murine Leukemia Virus (MMLVI reverse transcriptase of SEQ ID NO: 1.

* * * * *

SEQUENCE LISTING

```
Sequence total quantity: 15
SEQ ID NO: 1             moltype = AA  length = 671
FEATURE                  Location/Qualifiers
source                   1..671
                         mol_type = protein
                         organism = Murine leukemia virus
SEQUENCE: 1
TLNIEDEHRL HETSKEPDVS LGSTWLSDFP QAWAETGGMG LAVRQAPLII PLKATSTPVS   60
IKQYPMSQEA RLGIKPHIQR LLDQGILVPC QSPWNTPLLP VKKPGTNDYR PVQDLREVNK  120
RVEDIHPTVP NPYNLLSGLP PSHQWYTVLD LKDAFFCLRL HPTSQPLFAF EWRDPEMGIS  180
GQLTWTRLPQ GFKNSPTLFD EALHRDLADF RIQHPDLILL QYVDDLLLAA TSELDCQQGT  240
RALLQTLGNL GYRASAKKAQ ICQKQVKYLG YLLKEGQRWL TEARKETVMG QPTPKTPRQL  300
REFLGTAGFC RLWIPGFAEM AAPLYPLTKT GTLFNWGPDQ QKAYQEIKQA LLTAPALGLP  360
DLTKPFELFV DEKQGYAKGV LTQKLGPWRR PVAYLSKKLD PVAAGWPPCL RMVAAIAVLT  420
KDAGKLTMGQ PLVILAPHAV EALVKQPPDR WLSNARMTHY QALLLDTDRV QFGPVVALNP  480
ATLLPLPEEG LQHNCLDILA EAHGTRPDLT DQPLPDADHT WYTDGSSLLQ EGQRKAGAAV  540
TTETEVIWAK ALPAGTSAQR AELIALTQAL KMAEGKKLNV YTDSRYAFAT AHIHGEIYRR  600
RGLLTSEGKE IKNKDEILAL LKALFLPKRL SIIHCPGHQK GHSAEARGNR MADQAARKAA  660
ITETPDTSTL L                                                      671

SEQ ID NO: 2             moltype = AA  length = 704
FEATURE                  Location/Qualifiers
REGION                   1..704
                         note = Synthetic
source                   1..704
                         mol_type = protein
                         organism = synthetic construct
SEQUENCE: 2
MGGSHHHHHH GMASMTGGQQ MGRDLYDDDD KHMTLNIEDE HRLHETSKEP DVSLGSTWLS   60
DFPQAWAETG GMGLAVRQAP LIIPLKATST PVSIKQYPMS QEARLGIKPH IQRLLDQGIL  120
VPCQSPWNTP LLPVKKPGTN DYRPVQDLRE VNKRVEDIHP TVPNPYNLLS GLPPSHQWYT  180
VLDLKDAFFC LRLHPTSQPL FAFEWRDPEM GISGQLTWTR LPQGFKNSPT LFDEALHRDL  240
ADFRIQHPDL ILLQYVDDLL LAATSELDCQ QGTRALLQTL GNLGYRASAK KAQICQKQVK  300
YLGYLLKEGQ RWLTEARKET VMGQPTPKTP RQLREFLGTA GFCRLWIPGF AEMAAPLYPL  360
TKTGTLFNWG PDQQKAYQEI KQALLTAPAL GLPDLTKPFE LFVDEKQGYA KGVLTQKLGP  420
WRRPVAYLSK KLDPVAAGWP PCLRMVAAIA VLTKDAGKLT MGQPLVILAP HAVEALVKQP  480
PDRWLSNARM THYQALLLDT DRVQFGPVVA LNPATLLPLP EEGLQHNCLD ILAEAHGTRP  540
DLTDQPLPDA DHTWYTGGSS LLQEGQRKAG AAVTTETEVI WAKALPAGTS AQRAQLIALT  600
QALKMAEGKK LNVYTNSRYA FATAHIHGEI YRRRGLLTSE GKEIKNKDEI LALLKALFLP  660
KRLSIIHCPG HQKGHSAEAR GNRMADQAAR KAAITETPDT STLL                  704

SEQ ID NO: 3             moltype = DNA  length = 2115
FEATURE                  Location/Qualifiers
misc_feature             1..2115
                         note = Synthetic
source                   1..2115
                         mol_type = other DNA
                         organism = synthetic construct
SEQUENCE: 3
atgggggggtt ctcatcatca tcatcatcat ggtatggcta gcatgactgg tggacagcaa   60
atgggtcggg atctgtacga cgatgacgat aagcatatga ccctaaatat agaagatgag  120
caccggctac atgagacctc aaaagagcca gatgtttctc tagggtccac atggttatcg  180
gatttcccgc aagcttgggc tgaaacgggg ggtatggggc ttgctgtacg ccaggcgccc  240
cttattattc ctcttaaggc aacaagcacc ccgtcagca tcaaacaata ccccatgtca  300
caagaagcgc gtttgggtat taaaccgcac attcaacgct tgctggacca agggatcctt  360
gtccctgtc agtctccatg gaacacgccg ctgttaccgg tcaagaagcc tggtacaaac  420
gactaccgtc ctgtacagga tttgcgcgag gtaaataagc gtgtagagga tatccaccgc  480
accgtgccca acccatacaa cttgttgtct ggtttaccgc cttcacatca gtggtatacg  540
gtccttgatt tgaaagatgc attttttctgc ctgcgcttgc accctacgtc tcagccactg  600
ttcgcattcg agtggcgcga ccctgaaatg ggtatcagtg gtcagttaac ctggacacgc  660
ttaccgcaag gtttcaagaa tagcccgacc ttattgacga agcacttcag ccgcgatctt  720
gccgatttcc gcatccagca cccggatctt attttgttgc agtacgtaga cgacctgttg  780
ttggcagcca cgtcggaatt ggattgtcag caaggaacac gcgcgttact gcaaactctg  840
ggtaatttgg gctaccgtgc ctccgcaaag aaagcgcaga tctgccaaaa gcaagtaaaa  900
tacttaggat atttattgaa ggaggggcca cgttggctta cagaagctcg caaagaaact  960
gtgatgggac aacctacgcc taaaactcct cgtcagcttc gcgaattcct gggaacagcg 1020
gggttctgtc gcctgtggat tcctggtttt gcagagatgg cggcgcccct tacccactg 1080
accaaaacag gacattatt taactgggt cccgatcagc agaaggccta tcaggagatc 1140
aagcaggctt tacttacagc gccagccttatgggttaccgg accttacgaa gcccttttgag 1200
ttattcgtcg acgagaaaca gggctatgca aagggtgtac tgacccagaa gttggggccg 1260
tggcgtcgcc cggtcgccta tttgtcgaaa aaactggatc ccgtggcggc cgggtggcca 1320
ccttgcctgc gtatggttgc agctattgct gtattaacaa agacgcagg aaaattaacg 1380
atgggacaac cgttagtcat tcttgcgccg cacgcagtag aagcactggt aaagcaaccg 1440
cccgatcgct ggtatccgaa cgcgcgcatg acgcactatc aggcgttgtt acttgataca 1500
gatcgtgtac agtttggccc tgtcgttgca ttgaacccag ccacgctgtt acctcttccg 1560
gaagaaggat taacacaca ctgtctggac atcctggcgg aagctcatgg aaccgcccct 1620
gacttgacag accaaccgtt acccgacgct gatcatacct ggtataccgg gggttcgtcg 1680
cttttgcagg aagggcaacg taaggcaggt gcagccgtaa cgaccgagac cgaagtcatc 1740
```

```
tgggccaagg ccttgccagc ggggactagt gcccagcgtg cccaattaat tgcccttacg   1800
caggcattaa agatggctga aggaaaaaag ctgaatgtat acactaacag ccgctacgcg   1860
ttcgcgacag cgcatattca tggagagatc taccgtcgcc gcggacttct tacctccgag   1920
ggtaaggaga ttaagaacaa agatgagatt ctggctttgt tgaaggcgtt gttttttgccc  1980
aaacgtttgt caatcattca ctgtcccggg catcaaaaag ggcacagcgc cgaggcccgt   2040
ggtaaccgta tggcagacca ggccgcacgt aaagcagcca ttacggagac acctgatacg   2100
agtacgttac tttaa                                                    2115

SEQ ID NO: 4              moltype = AA   length = 716
FEATURE                   Location/Qualifiers
REGION                    1..716
                          note = Synthetic
source                    1..716
                          mol_type = protein
                          organism = synthetic construct
SEQUENCE: 4
MGGSHHHHHH GMASMTGGQQ MGRDLYDDDD KHMTLNIEDE HRLHETSKEP DVSLGSTWLS    60
DFPQAWAETG GMGLAVRQAP LIIPLKATAT PVSIKQYPMS QEARQGIKPH IQRLLDQGIL   120
VPCQSPWNTP LLPVKKPGTN DYRPVQDLRE VNKRVEDIHP TVPNPYNLLS SLPPSHQWYT   180
VLDLKDAFFC LRLHPKSQPL FAFEWRDPEM GISGQLTWTR LPQGFKNSPT LFDEALRRDL   240
ADFRIQHPDL ILLQYVDDLL LAATTEEDCQ QGTRALLQTL GELGYRASAK KAQICQKQVK   300
YLGYLLKEGQ RWLTEARKET VMKQPTPKTP RQLREFLGKA GFCRLWIPGF AEMAAPLYPL   360
TKTGTLFNWG PDQQKAFQEI KQALLTAPAL GLPDLTKPFE LFVDEKQGYA KGVLTQKLGP   420
WRRPVAYLSK KLDPVAAGWP PCLRMVAAIA VLVKDADKLT MGQPLVILAP HAVEALIKQP   480
PDRWLSNARM THYQALLLDT DRVQFGPVVA LNPATLLPLP EEGLQHNCLD ILAEAHGTRP   540
DLTDQPLPDA DHTWYTGSSS LLQEGQRKAG AAVTTETEVI WAKALPAGTS AQRAQLIALT   600
QALKMAEGKK LNVYTNSRYA FATAHIHGEI YRRRGLLTSE GKEIKNKEEI LALLKALFLP   660
KRLSIIHCPG HQKGDSAEAR GNRMADQAAR KAAITETPDT STLLIENSSP NSRLIN       716

SEQ ID NO: 5              moltype = AA   length = 717
FEATURE                   Location/Qualifiers
REGION                    1..717
                          note = Synthetic
source                    1..717
                          mol_type = protein
                          organism = synthetic construct
SEQUENCE: 5
MGGSHHHHHH GMASMTGGQQ MGRDLYDDDD KHMTLNIEDE HRLHETSKEP DVSLGSMTWL    60
SDFPQAWAET GGMGLAVRQA PLIIPLKATA TPVSIKQYPM SQEARLGIKP HIQRLLDQGI   120
LVPCQSPWNT PLLPVKKPGT NDYRPVQDLR EVNKRVEDIH PTVPNPYNLL SSLPPSHQWY   180
TVLDLKDAFF CLRLHPTSQP LFAFEWRDPE MGISGQLTWT RLPQGFKNSP TLFDEALHRD   240
LADFRIQHPD LILLQYVDDL LLAATTEEDC QQGTRALLQT LGNLGYRASA KKAQICQKQV   300
KYLGYLLKEG QRWLTEARKE TVMKQPTPKT PRQLREFLGT AGFCRLWIPG FAEMAAPLYP   360
LTKTGTLFNW GPDQQKAFQE IKQALLTAPA LGLPDLTKPF ELFVDEKQGY AKGVLTQKLG   420
PWRRPVAYLS KKLDPVAAGW PPCLRMVAAI AVLVKDADKL TMGQPLVILA PHAVEALIKQ   480
PPDRWLSNAR MTHYQALLLD TDRVQFGPVV ALNPATLLPL PEEGLQHNCL DILAEAHGTR   540
PDLTDQPLPD ADHTWYTGSS LLQEGQRKA GAAVTTETEVI WAKALPAGT SAQRAQLIAL   600
TQALKMAEGK KLNVYTNSRY AFATAHIHGE IYRRRGLLTS EGKEIKNKEE ILALLKALFL   660
PKRLSIIHCP GHQKGHSAEA RGNRMADQAA RKAAITETPD TSTLLIENSS PNSRLIN      717

SEQ ID NO: 6              moltype = AA   length = 716
FEATURE                   Location/Qualifiers
REGION                    1..716
                          note = Synthetic
source                    1..716
                          mol_type = protein
                          organism = synthetic construct
SEQUENCE: 6
MGGSHHHHHH GMASMTGGQQ MGRDLYDDDD KHMTLNIEDE HRLHETSKEP DVSLGSTWLT    60
DFPQAWAETG GMGLAKRQPP IIIPLKPTAT PVWIKQYPMS KEARQGIKPH IQRLLDQGIL   120
VPCQSPWNTP LLPVKKPGTN DYRPVQDLRE VNKRVQDIHP TVPNPCNLLS SLPPSHQWYT   180
VLDLKDAFFC LRLHPKSQPL FAFEWRDPER GISGQLTWTR LPQGFKNSPT LFHEALHRDL   240
ADFRTQHPDL TLLQYVDDLL LAAETEEDCE QGTRDLLQT AGFCRLWIPGF AEMAAPLYPL   300
YLGYILKEGQ RWLSEARKET VMKQPTPKTP RQLREFLGTA GFCRLWIPGF AEMAAPLYPL   360
TKTGTLFQWG EEQQKAFDDI KRALLTAPAL GLPDLTKPFE LFVDEKQGFA KGVLTQKLGP   420
WRRPVAYLSK KLDPVAAGWP PCLRMIAAIA VLVKDADKLT MGQPLTILAP HAVESLIKQP   480
PDRWLSNARM THYQALLLDT DRVQFGPVVA LNPATLLPLP EEGLQHNCLD ILAEAHGTRP   540
DLTDQPLPDA EHTWYTGSSS FLQEGQRKAG AAVTTETEVI WASALPPGTS AQRAQLIALT   600
QALKMAEGKK LNVYTNSRYA FATAHIHGEI YRRRGLLTSE GKEIKNKEEI LELLKALWLP   660
KKLAIIHCPG HQKGDSAEAR GNRMADQAAR EAAITETPDT STLLIENSSP NSRLIN       716

SEQ ID NO: 7              moltype = AA   length = 717
FEATURE                   Location/Qualifiers
REGION                    1..717
                          note = Synthetic
source                    1..717
                          mol_type = protein
                          organism = synthetic construct
SEQUENCE: 7
```

```
MGGSHHHHHH GMASMTGGQQ MGRDLYDDDD KHMTLNIEDE HRLHETSKEP DVSLGSMTWL    60
SDFPQAWAET GGMGLAVRQA PLIIPLKATA TPVSIKQYPM SQEARLGIKP HIQRLLDQGI   120
LVPCQSPWNT PLLPVKKPGT NDYRPVQDLR EVNKRVEDIH PTVPNPYNLL SSLPPSHQWY   180
TVLDLKDAFF CLRLHPTSQP LFAFEWRDPE MGISGQLTWT RLPQGFKNSP TLFDEALRRD   240
LADFRIQHPD LILLQYVDDL LLAATTEEDC QQGTRALLQT LGNLGYRASA KKAQICQKQV   300
KYLGYLLKEG QRWLTEARKE TVMKQPTPKT PRQLREFLGK AGFCRLWIPG FAEMAAPLYP   360
LTKTGTLFNW GPDQQKAFQE IKQALLTAPA LGLPDLTKPF ELFVDEKQGY AKGVLTQKLG   420
PWRRPVAYLS KKLDPVAAGW PPCLRMVAAI AVLVKDADKL TMGQPLVILA PHAVEALIKQ   480
PPDRWLSNAR MTHYQALLLD TDRVQFGPVV ALNPATLLPL PEEGLQHNCL DILAEAHGTR   540
PDLTDQPLPD ADHTWYTGGS SLLQEGQRKA GAAVTTETEV IWAKALPAGT SAQRAQLIAL   600
TQALKMAEGK KLNVYTNSRY AFATAHIHGE IYRRRGLLTS EGKEIKNKEE ILALLKALFL   660
PKRLSIIHCP GHQKGHSAEA RGNRMADQAA RKAAITETPD TSTLLIENSS PNSRLIN     717

SEQ ID NO: 8            moltype = AA   length = 716
FEATURE                 Location/Qualifiers
REGION                  1..716
                        note = Synthetic
source                  1..716
                        mol_type = protein
                        organism = synthetic construct
SEQUENCE: 8
MGGSHHHHHH GMASMTGGQQ MGRDLYDDDD KHMTLNIEDE HRLHETSKEP DVSLGSTWLS    60
DFPQAWAETG GMGLAKRQAP LIIPLKATAT PVSIKQYPMS QEARQGIKPH IQRLLDQGIL   120
VPCQSPWNTP LLPVKKPGTN DYRPVQDLRE VNKRVEDIHP TVPNPYNLLS SLPPSHQWYT   180
VLDLKDAFFC LRLHPTSQPL FAFEWRDPEM GISGQLTWTR LPQGFKNSPT LFDEALRRDL   240
ADFRIQHPDL ILLQYVDDLL LAATTEEDCE QGTRALLQTL GELGYRASAK KAQICQKEVK   300
YLGYLLKEGQ RWLTEARKET VMKQPTPKTP RQLREFLGKA GFCRLWIPGF AEMAAPLYPL   360
TKTGTLFNWG PDQQKAFQEI KQALLTAPAL GLPDLTKPFE LFVDEKQGVA KGVLTQKLGP   420
WRRPVAYLSK KLDPVAAGWP PCLRMVAAIA VLVKDADKLT MGQPLVILAP HAVEALIKQP   480
PDRWLSNARM THYQALLLDT DRVQFGPVVA LNPATLLPLP EEGLQHNCLD ILAEAHGTRP   540
DLTDQPLPDA DHTWYTGGSS FLQEGQRKAG AAVTTETEVI WAKALPAGTS AQRAQLIALT   600
QALKMAEGKK LNVYTNSRYA FATAHIHGEI YRRRGLLTSE GKEIKNKEEI LALLKALFLP   660
KRLSIIHCPG HQKGDSAEAR GNRMADQAAR KAAITETPDT STLLIENSSP NSRLIN      716

SEQ ID NO: 9            moltype = AA   length = 717
FEATURE                 Location/Qualifiers
REGION                  1..717
                        note = Synthetic
source                  1..717
                        mol_type = protein
                        organism = synthetic construct
SEQUENCE: 9
MGGSHHHHHH GMASMTGGQQ MGRDLYDDDD KHMTLNIEDE HRLHETSKEP DVSLGSMTWL    60
SDFPQAWAET GGMGLAVRQA PLIIPLKATA TPVSIKQYPM SQEARLGIKP HIQRLLDQGI   120
LVPCQSPWNT PLLPVKKPGT NDYRPVQDLR EVNKRVEDIH PTVPNPYNLL SSLPPSHQWY   180
TVLDLKDAFF CLRLHPTSQP LFAFEWRDPE MGISGQLTWT RLPQGFKNSP TLFDEALRRD   240
LADFRIQHPD LILLQYVDDL LLAATTEEDC QQGTRALLQT LGNLGYRASA KKAQICQKQV   300
KYLGYLLKEG QRWLTEARKE TVMKQPTPKT PRQLREFLGK AGNCRLWIPG FAEMAAPLYP   360
LTKTGTLFNW GPDQQKAFQE IKQALLTAPA LGLPDLTKPF ELFVDEKQGY AKGVLTQKLG   420
PWRRPVAYLS KKLDPVAAGW PPCLRMVAAI AVLVKDADKL TMGQPLVILA PHAVEALIKQ   480
PPDRWLSNAR MTHYQALLLD TDRVQFGPVV ALNPATLLPL PEEGLQHNCL DILAEAHGTR   540
PDLTDQPLPD ADHTWYTGGS SLLQEGQRKA GAAVTTETEV IWAKALPAGT SAQRAQLIAL   600
TQALKMAEGK KLNVYTNSRY AFATAHIHGE IYRRRGLLTS EGKEIKNKEE ILALLKALFL   660
PKRLSIIHCP GHQKGHSAEA RGNRMADQAA RKAAITETPD TSTLLIENSS PNSRLIN     717

SEQ ID NO: 10           moltype = AA   length = 716
FEATURE                 Location/Qualifiers
REGION                  1..716
                        note = Synthetic
source                  1..716
                        mol_type = protein
                        organism = synthetic construct
SEQUENCE: 10
MGGSHHHHHH GMASMTGGQQ MGRDLYDDDD KHMTLNIEDE HRLHETSKEP DVSLGSTWLS    60
DFPQAWAETG GMGLAVRQAP LIIPLKATAT PVSIKQYPMS QEARQGIKPH IQRLLDQGIL   120
VPCQSPWNTP LLPVKKPGTN DYRPVQDLRE VNKRVEDIHP TVPNPYNLLS SLPPSHQWYT   180
VLDLKDAFFC LRLHPTSQPL FAFEWRDPEM GISGQLTWTR LPQGFKNSPT LFDEALRRDL   240
ADFRIQHPDL ILLQYVDDLL LAATTEEDCQ QGTRALLQTL GELGYRASAK KAQICQKVK    300
YLGYLLKEGQ RWLTEARKET VMKQPTPKTP RQLREFLGKA GNCRLWIPGF AEMAAPLYPL   360
TKTGTLFNWG PDQQKAFQEI KQALLTAPAL GLPDLTKPFE LFVDEKQGYA KGVLTQKLGP   420
WRRPVAYLSK KLDPVAAGWP PCLRMVAAIA VLVKDADKLT MGQPLVILAP HAVEALIKQP   480
PDRWLSNARM THYQALLLDT DRVQFGPVVA LNPATLLPLP EEGLQHNCLD ILAEAHGTRP   540
DLTDQPLPDA DHTWYTGGSS LLQEGQRKAG AAVTTETEVI WAKALPAGTS AQRAQLIALT   600
QALKMAEGKK LNVYTNSRYA FATAHIHGEI YRRRGLLTSE GKEIKNKEEI LALLKALFLP   660
KRLSIIHCPG HQKGDSAEAR GNRMADQAAR KAAITETPDT STLLIENSSP NSRLIN      716

SEQ ID NO: 11           moltype = AA   length = 716
FEATURE                 Location/Qualifiers
REGION                  1..716
```

```
                        note = Synthetic
source                  1..716
                        mol_type = protein
                        organism = synthetic construct
SEQUENCE: 11
MGGSHHHHHH GMASMTGGQQ MGRDLYDDDD KHMTLNIEDE HRLHETSKEP DVSLGSTWLT    60
DFPQAWAETG GMGLAKRQPP IIIPLKPTAT PVWIKQYPMS KEARQGIKPH IQRLLDQGIL   120
VPCQSPWNTP LLPVKKPGTN DYRPVQDLRE VNKRVQDIHP TVPNPCNLLS SLPPSHQWYT   180
VLDLKDAFFC LRLHPKSQPL FAFEWRDPER GISGQLTWTR LPQGFKNSPT LFHEALRRDL   240
ADFRTQHPDL TLLQYVDDLL LAAETEEDCE QGTRDLLQTL GELGYRASAK KAQICQQEVT   300
YLGYILKEGQ RWLSEARKET VMKQPTPKTP RQLREFLGKA GFCRLWIPGF AEMAAPLYPL   360
TKTGTLFQWG EEQQKAFDDI KRALLTAPAL GLPDLTKPFE LFVDEKQGFA KGVLTQKLGP   420
WRRPVAYLSK KLDPVAAGWP PCLRMIAAIA VLVKDADKLT MGQPLTILAP HAVESLIKQP   480
PDRWLSNARM THYQALLLDT DRVQFGPVVA LNPATLLPLP EEGLQHNCLD ILAEAHGTRP   540
DLTDQPLPDA EHTWYTGGSS FLQEGQRKAG AAVTTETEVI WASALPPGTS AQRAQLIALT   600
QALKMAEGKK LNVYTNSRYA FATAHIHGEI YRRRGLLTSE GKEIKNKEEI LELLKALWLP   660
KKLAIIHCPG HQKGDSAEAR GNRMADQAAR EAAITETPDT STLLIENSSP NSRLIN       716

SEQ ID NO: 12           moltype = AA  length = 716
FEATURE                 Location/Qualifiers
REGION                  1..716
                        note = Synthetic
source                  1..716
                        mol_type = protein
                        organism = synthetic construct
SEQUENCE: 12
MGGSHHHHHH GMASMTGGQQ MGRDLYDDDD KHMTLNIEDE HRLHETSKEP DVSLGSTWLT    60
DFPQAWAETG GMGLAKRQPP IIIPLKPTAT PVWIKQYPMS KEARQGIKPH IQRLLDQGIL   120
VPCQSPWNTP LLPVKKPGTN DYRPVQDLRE VNKRVQDIHP TVPNPCNLLS SLPPSHQWYT   180
VLDLKDAFFC LRLHPKSQPL FAFEWRDPER GISGQLTWTR LPQGFKNSPT LFHEALRRDL   240
ADFRTQHPDL TLLQYVDDLL LAAETEEDCE QGTRDLLQTL GELGYRASAK KAQICQQEVT   300
YLGYILKEGQ RWLSEARKET VLKQPTPKTP RQLREFLGKA GNCRLWIPGF AEMAAPLYPL   360
TKTGTLFQWG EEQQKAFDDI KRALLTAPAL GLPDLTKPFE LFVDEKQGFA KGVLTQKLGP   420
WRRPVAYLSK KLDPVAAGWP PCLRMIAAIA VLVKDADKLT MGQPLTILAP HAVESLIKQP   480
PDRWLSNARM THYQALLLDT DRVQFGPVVA LNPATLLPLP EEGLQHNCLD ILAEAHGTRP   540
DLTDQPLPDA EHTWYTGGSS FLQEGQRKAG AAVTTETEVI WASALPPGTS AQRAQLIALT   600
QALKMAEGKK LNVYTNSRYA FATAHIHGEI YRRRGLLTSE GKEIKNKEEI LELLKALWLP   660
KKLAIIHCPG HQKGDSAEAR GNRMADQAAR EAAITETPDT STLLIENSSP NSRLIN       716

SEQ ID NO: 13           moltype = AA  length = 716
FEATURE                 Location/Qualifiers
REGION                  1..716
                        note = Synthetic
source                  1..716
                        mol_type = protein
                        organism = synthetic construct
SEQUENCE: 13
MGGSHHHHHH GMASMTGGQQ MGRDLYDDDD KHMTLNIEDE HRLHETSKEP DVSLGSTWLS    60
DFPQAWAETG GMGLAKRQAP LIIPLKPTAT PVWIKQYPMS QEARQGIKPH IQRLLDQGIL   120
VPCQSPWNTP LLPVKKPGTN DYRPVQDLRE VNKRVEDIHP TVPNPYNLLS SLPPSHQWYT   180
VLDLKDAFFC LRLHPKSQPL FAFEWRDPEM GISGQLTWTR LPQGFKNSPT LFHEALRRDL   240
ADFRIQHPDL ILLQYVDDLL LAATTEEDCE QGTRALLQTL GELGYRASAK KAQICQKEVT   300
YLGYLLKEGQ RWLTEARKET VMKQPTPKTP RQLREFLGTA GFCRLWIPGF AEMAAPLYPL   360
TKTGTLFNWG PEQQKAFQEI KQALLTAPAL GLPDLTKPFE LFVDEKQGFA KGVLTQKLGP   420
WRRPVAYLSK KLDPVAAGWP PCLRMVAAIA VLVKDADKLT MGQPLTILAP HAVEALIKQP   480
PDRWLSNARM THYQALLLDT DRVQFGPVVA LNPATLLPLP EEGLQHNCLD ILAEAHGTRP   540
DLTDQPLPDA DHTWYTGGSS FLQEGQRKAG AAVTTETEVI WAKALPPGTS AQRAQLIALT   600
QALKMAEGKK LNVYTNSRYA FATAHIHGEI YRRRGLLTSE GKEIKNKEEI LALLKALWLP   660
KRLSIIHCPG HQKGDSAEAR GNRMADQAAR EAAITETPDT STLLIENSSP NSRLIN       716

SEQ ID NO: 14           moltype = AA  length = 704
FEATURE                 Location/Qualifiers
REGION                  1..704
                        note = Synthetic
source                  1..704
                        mol_type = protein
                        organism = synthetic construct
SEQUENCE: 14
MGGSHHHHHH GMASMTGGQQ MGRDLYDDDD KHMTLNIEDE HRLHETSKEP DVSLGSTWLS    60
DFPQAWAETG GMGLAVRQAP LIIPLKATST PVSIKQYPMS QEARLGIKPH IQRLLDQGIL   120
VPCQSPWNTP LLPVKKPGTN DYRPVQDLRE VNKRVEDIHP TVPNPYNLLS GLPPSHQWYT   180
VLDLKDAFFC LRLHPTSQPL FAFEWRDPEM GISGQLTWTR LPQGFKNSPT LFDEALRRDL   240
ADFRIQHPDL ILLQYVDDLL LAATSELDCQ QGTRALLQTL GNLGYRASAK KAQICQKEVK   300
YLGYLLKEGQ RWLTEARKET VMGQPTPKTP RQLREFLGKA GNCRLWIPGF AEMAAPLYQL   360
TKTGTLFNWG PDQQKAYQEI KQALLTAPAL GLPDLTKPFE LFVDEKQGYA KGVLTQKLGP   420
WRRPVAYLSK KLDPVAAGWP PCLRMVAAIA VLTKDAGKLT MGQPLVILAP HAVEALVKQP   480
PDRWLSNARM THYQALLLDT DRVQFGPVVA LNPATLLPLP EEGLQHNCLD ILAEAHGTRP   540
DLTDQPLPDA DHTWYTGGSS LLQEGQRKAG AAVTTETEVI WAKALPAGTS AQRAQLIALT   600
QALKMAEGKK LNVYTNSRYA FATAHIHGEI YRRRGLLTSE GKEIKNKDEI LALLKALFLP   660
```

```
KRLSIIHCPG HQKGHSAEAR GNRMADQAAR KAAITETPDT STLL                 704

SEQ ID NO: 15           moltype = AA  length = 716
FEATURE                 Location/Qualifiers
REGION                  1..716
                        note = Synthetic
source                  1..716
                        mol_type = protein
                        organism = synthetic construct
SEQUENCE: 15
MGGSHHHHHH GMASMTGGQQ MGRDLYDDDD KHMTLNIEDE HRLHETSKEP DVSLGSTWLS  60
DFPQAWAETG GMGLAVRQAP LIIPLKATST PVSIKQYPMS QEARQGIKPH IQRLLDQGIL 120
VPCQSPWNTP LLPVKKPGTN DYRPVQDLRE VNKRVEDIHP TVPNPYNLLS SLPPSHQWYT 180
VLDLKDAFFC LRLHPKSQPL FAFEWRDPEM GISGQLTWTR LPQGFKNSPT LFDEALHRDL 240
ADFRIQHPDL ILLQYVDDLL LAATTEEDCQ QGTRALLQTL GELGYRASAK KAQICQKQVK 300
YLGYLLKEGQ RWLTEARKET VMKQPTPKTP RQLREFLGTA GFCRLWIPGF AEMAAPLYPL 360
TKTGTLFNWG PDQQKAFQEI KQALLTAPAL GLPDLTKPFE LFVDEKQGYA KGVLTQKLGP 420
WRRPVAYLSK KLDPVAAGWP PCLRMVAAIA VLVKDADKLT MGQPLVILAP HAVEALIKQP 480
PDRWLSNARM THYQALLLDT DRVQFGPVVA LNPATLLPLP EEGLQHNCLD ILAEAHGTRP 540
DLTDQPLPDA DHTWYTGGSS LLQEGQRKAG AAVTTETEVI WAKALPAGTS AQRAQLIALT 600
QALKMAEGKK LNVYTNSRYA FATAHIHGEI YRRRGLLTSE GKEIKNKEEI LALLKALFLP 660
KRLSIIHCPG HQKGDSAEAR GNRMADQAAR KAAITETPDT STLLIENSSP NSRLIN    716
```